US011577296B2

(12) United States Patent
Plancher et al.

(10) Patent No.: US 11,577,296 B2
(45) Date of Patent: Feb. 14, 2023

(54) DEVICES AND METHODS FOR HOLDING A SAMPLE FOR MULTI-AXIAL TESTING

(71) Applicant: Massachusetts Institute of Technology, Cambridge, MA (US)

(72) Inventors: Emeric Plancher, Saint-Etienne (FR); Cemal Cem Tasan, Cambridge, MA (US); Nicolaas Hendrikus Vonk, Utrecht (NL); Ke Qu, Lanzhou (CN)

(73) Assignee: Massachusetts Institute of Technology, Cambridge, MA (US)

( * ) Notice: Subject to any disclaimer, the term of this patent is extended or adjusted under 35 U.S.C. 154(b) by 718 days.

(21) Appl. No.: 16/299,746

(22) Filed: Mar. 12, 2019

(65) Prior Publication Data

US 2019/0277738 A1  Sep. 12, 2019

Related U.S. Application Data

(60) Provisional application No. 62/641,961, filed on Mar. 12, 2018.

(51) Int. Cl.
*B21D 26/021* (2011.01)
*G01N 3/04* (2006.01)
*G01N 3/10* (2006.01)

(52) U.S. Cl.
CPC .............. *B21D 26/021* (2013.01); *G01N 3/04* (2013.01); *G01N 3/10* (2013.01); *G01N 2203/0026* (2013.01); *G01N 2203/0048* (2013.01)

(58) Field of Classification Search
CPC ................ B21D 26/021; B21D 26/031; B21D 26/029; G01N 3/04; G01N 3/10; G01N 3/12;

(Continued)

(56) References Cited

U.S. PATENT DOCUMENTS 3,726,597 A * 4/1973 Dvorak ................. C12M 41/36
356/244
4,242,586 A * 12/1980 Warble .................... H01J 37/20
250/443.1

(Continued)

FOREIGN PATENT DOCUMENTS

JP  2013235778 A  * 11/2013

OTHER PUBLICATIONS

Wang et al., "Property-adjustable forming medium induced extension of sheet metal formability under variable magnetic field", Journal of Materials Processing Technology, vol. 243, May 2017, pp. 420-432, <https://www.sciencedirect.com/science/article/pii/S092401361730002X> (Year: 2017).*

(Continued)

*Primary Examiner* — Jonathan M Dunlap
(74) *Attorney, Agent, or Firm* — Nutter McClennen & Fish LLP

(57) ABSTRACT

Methods and devices are disclosed for tracking site-specific microstructure evolutions and local mechanical fields in metallic samples deformed along biaxial strain paths. The method is based on interrupted bulge tests carried out with a custom sample holder adapted for SEM-based analytical measurements. Embodiments include elliptical dies used to generate proportional and complex strain paths in material samples. One example holding device includes a base having a floor and walls that extend to form a chamber for a sample, the floor having apertures for receiving a pressure-supplying fluid, a cover having an opening and configured such that the cover and base can be coupled together to tightly clamp a sample in the chamber, and washers disposed between the base and the cover, each washer having openings extending therethrough change at least one of a shape and a size of the opening formed in the cover.

20 Claims, 13 Drawing Sheets

(58) Field of Classification Search
CPC .............. G01N 2203/0026; G01N 2203/0048;
G01N 2203/0042; G01N 2203/0044
See application file for complete search history.

(56) References Cited

U.S. PATENT DOCUMENTS

| | | | | |
|---|---|---|---|---|
| 4,596,934 | A * | 6/1986 | Yanaka | H01J 37/20 |
| | | | | 250/442.11 |
| 5,821,544 | A * | 10/1998 | Augustus | H01J 37/20 |
| | | | | 250/440.11 |
| 6,539,790 | B2 * | 4/2003 | Huston | G01N 3/04 |
| | | | | 73/150 A |
| 10,670,501 | B2 * | 6/2020 | Jelokhani Niaraki | G01N 3/28 |
| 2002/0066311 | A1 * | 6/2002 | Huston | G01N 3/04 |
| | | | | 73/159 |
| 2010/0018320 | A1 * | 1/2010 | Shuaib | B21D 22/20 |
| | | | | 73/799 |
| 2016/0154926 | A1 * | 6/2016 | Szigeti | G06T 7/32 |
| | | | | 703/8 |
| 2018/0067028 | A1 * | 3/2018 | Jelokhani Niaraki | G01N 3/28 |
| 2021/0041319 | A1 * | 2/2021 | Liang | G01N 3/04 |

OTHER PUBLICATIONS

Alaie, A et al., "Effect of microstructure pattern on the strain localization in DP600 steels analyzed using combined in-situ experimental test and numerical simulation.", Materials Science and Engineering: A, vol. 638, pp. 251-261, Jun. 25, 2015 (11 pages).
Archie, F et al., "Micro-damage initiation in ferrite-martensite DP microstructures: A statistical characterization of crystallographic and chemical parameters.", Materials Science and Engineering: A, vol. 701, pp. 302-313, Jul. 31, 2017 (12 pages).
Avramovic-Cingara, G et al., "Void Nucleation and Growth in Dual-Phase Steel 600 during Uniaxial Tensile Testing.", Metallurgical and Materials Transactions A, vol. 40, Issue 13, pp. 3117-3127, Dec. 2009 (11 pages).
Banabic, D et al., "Formability of Metallic Materials.", 2000 (345 pages).
Bareggi, A et al., "Damage in dual phase steels and its constituents studied by X-ray tomography.", International Journal of Fracture, vol. 174, Issue 2, pp. 217-227, Apr. 2012 (11 pages).
Britton, T.B. et al., "Stress fields and geometrically necessary dislocation density distributions near the head of a blocked slip band.", Acta Materialia, vol. 60, Issue 16, pp. 5773-5782, Sep. 2012 (10 pages).
Bouaziz, O et al, "Driving force and logic of development of advanced high strength steels for automotive applications.", Steel Research International, vol. 84, Issue 10, pp. 937-947, 2013 (11 pages).
Caër, C et al., "Local behavior of an AISI 304 stainless steel submitted to in situ biaxial loading in SEM.", Materials Science and Engineering: A, vol. 690, p. 44-51, Apr. 6, 2017 (8 pages).
Chen, K et al., "Effects of anisotrophy on material hardening and burst in the bulge test." International Journal of Solids and Structures, vol. 82, pp. 70-84, 2016 (15 pages).
Franz, G et al., "Role of intragranular microstructure development in the macroscopic behavior of multiphase steels in the context of changing strain paths.", Materials Science and Engineering: A, vol. 517, Issues 1-2, pp. 300-311, Aug. 20, 2009 (12 pages).
Gardey, B et al., "Texture and dislocation strcutures observation in a dual-phase steel under strain-path changes at large deformation.", Materials Science and Engineering: A, vols. 400-401, pp. 136-141, Jul. 25, 2005 (6 pages).
Ghadbeigi, H et al., "Failure mechanisms in DP600 steel: Initiation, evolution and fracture.", Materials Science and Engineering: A, vol. 588, pp. 420-431, Dec. 20, 2013 (12 pages).
Gorji, M.B. et al., "Micro-tension and micro-shear experiments to characterize stress-state dependent ductile fracture.", Acta Materialia, vol. 131, pp. 65-76, Jun. 1, 2017 (12 pages).

Ha, J et al., "Investigation of plastic strain rate under strain path changes in dual-phase steel using microstructure-based modeling.", International Journal of Plasticity, pp. 1-23, Jun. 2017 (23 pages).
Hoefnagels, J.P.M. et al., "Retardation of plastic instability via damage-enabled microstrain delocalization.", Journal of Materials Science, vol. 50, Issue 21, pp. 6882-6897, Nov. 2015 (17 pages).
Jayyosi, C et al., "Geometry of an inflated membrane in elliptic bulge tests: Evaluation of an ellipsoidal shape approximation by stereoscopic digital image correlation measurements.", Medical Engineering & Physics, pp. 1-8, 2017 (8 pages).
Kadkhodapur, J et al., "Mechanisms of void formation during tensile testing in a commerical, dual-phase steel.", Acta Materialia, vol. 59, Issue 7, pp. 2575-2588, Apr. 2011 (14 pages).
Kamaya, M et al., "Measurement of plastic strain of polycrystalline material by electron backscatter diffraction.", Nuclear Engineering and Design, vol. 235, Issue 6, pp. 713-725, Mar. 2005 (13 pages).
Kang, J et al., "Digital image correlation studies for microscopic strain distribution and damage in dual phase steels.", Scipta Materialia, vol. 56, Issue 11, pp. 999-1002, Jun. 2007 (4 pages).
Kikuma, T et al., "Effects of deforming conditions and mechanical properties on the stretch forming limits of steel sheets.", Transactions of the Iron and Steel Institute of Japan, vol. 11, pp. 827-831, 1971 (7 pages).
Kubo, M et al., "Development of Biaxial Tensile Test System for In-situ Scanning Electron Microscope and Electron Backscatter Diffraction Analysis.", vol. 56, Issue 4, pp. 669-677, 2016 (9 pages).
Lian, J et al., "A method to quantitatively upscale the damage initiation of dual-phase steels under various stress states from microscale to macroscale.", Computational Materials Science, vol. 94, pp. 245-257, Nov. 2014 (13 pages).
Liao, J et al., "Mechanical, microstructural behaviour and modelling of dual phase steels under complex deformation paths.", International Journal of Plasticity, pp. 1-22, 2016 (22 pages).
Livescu, V et al., "Biaxial deformation in high purity aluminum.", Materials Science and Engineering: A, vol. 648, pp. 330-339, Nov. 11, 2015 (10 pages).
Maire, E et al., "Initiation and growth of damage in a dual-phase steel observed by X-ray microtomography.", Acta Materialia, vol. 56, Issue 18, pp. 4954-4964, Oct. 2008 (11 pages).
Marcadet, S.J. et al., "Effect of compression-tension loading reversal on the strain to fracture of dual phase steel sheets.", International Journal of Plasticity, vol. 72, pp. 21-43, 2015 (23 pages).
Matsuno, T et al., "Mesoscale simulation of the early evolution of ductile fracture in dual-phase steels.", International Journal of Plasticity, vol. 74, pp. 17-34, 2015 (18 pages).
Min, J et al., "Accurate characterization of biaxial stress-strain response of sheet metal from bulge testing.", International Journal of Plasticity, vol. 94, pp. 1921-213, 2017 (22 pages).
Mulder, J et al., "Accurate determination of flow curves using the bulge test with optical measuring systems.", Journal of Materials Processing Technology, vol. 226, pp. 169-187, Dec. 2015 (19 pages).
Neggers, J et al., "Direct Stress-Strain Measurements from Bulged Membranes using Topography Image Correlation.", Experimental Mechanics, vol. 54, Issue 5, pp. 717-727, Jun. 2014 (11 pages).
Pantleon, W, "Resolving the geometrically necessary dislocation content by conventional electron backscattering diffraction.", Scripta Materialia, vol. 58, Issue 11, pp. 994-997, Jun. 2008 (4 pages).
Paul, O et al., "Thin-Film Characterization using the Bulge Test.", Reliability of MEMS: Testing of Materials and Devices, pp. 67-121, 2008 (56 pages).
Plancher, E et al., "Tracking Microstructure Evolution in Complex Biaxial Strain Paths: A Bulge Test Methodology for the Scanning Electron Microscope.", Experimental Mechanics, pp. 1-16, 2019 (18 pages).
Plancher, E et al., "On the Accuracy of the Elastic Strain Field Measurements by Laue Microdiffraction and High-Resolution EBSD: a Cross-Validation Experiment.", Experimental Mechanics, vol. 56, Issue 3, pp. 483-492, 2016 (10 pages).
Ram, F et al., "On the origin of creep dislocations in a Ni-base, single-crystal superalloy: An ECCI, EBSD, and disclocation dynamics-based study.", Acta Materialia, vol. 109, pp. 151-161, 2016 (11 pages).

(56) References Cited

OTHER PUBLICATIONS

Reis, L.C. et al., "Anisotrophy and plastic flow in the circular bulge test.", International Journal of Mechanical Sciences, vols. 128-129, pp. 70-93, 2017 (24 pages).

Suttner, S et al., "Experimental and numerical investigation of a strain rate controlled hydraulic bulge test of sheet metal.", Journal of Materials Processing Technology, vol. 235, pp. 121-133, 2016 (13 pages).

Sutton, M.A. et al., "Scanning electron microscopy for quantitative small and large deformation measurements Part I: SEM imaging at magnifications from 200 to 10,000.", Experimental Mechanics, vol. 47, Issue 6, pp. 775-787, 2007 (13 pages).

Tasan, C.C. et al., "An Overview of Dual-Phase Steels: Advances in Microstructure-Oriented Processing and Micromechanically Guided Design.", Annual Review of Materials Research, vol. 45, Issue 1, pp. 391-431, 2015 (41 pages).

Tasan, C.C. et al., "Experimental analysis of strain path dependent ductile damage mechanics and forming limits.", Mechanics of Materials, vol. 41, Issue 11, pp. 1264-1276, 2009 (13 pages).

Tasan, C.C. et al., "Multi-Axial Deformation Setup for Microscopic Testing of Sheet Metal to Fracture.", Experimental Mechanics, vol. 52, Issue 7, pp. 669-678, 2012 (10 pages).

Tasan, C.C. et al., "Microstructual banding effects claified through micrographic digital image correlation.", Scripta Materialia, vol. 62, Issue 11, pp. 835-838, 2010 (4 pages).

Tatschl, A et al., "On the experimental characterization of crystal plasticity in polycrystals.", Materials Science and Engineering: A, vol. 356, pp. 447-463, 2003 (17 pages).

Tonge, T.K. et al., "Full-field bulge test for planar anisotropic tissues: Part I-Experimental methods applied to human skin tissue.", Acta Biomaterialia, vol. 9, Issue 4, pp. 5913-5925, 2013 (13 pages).

Torres, E.A. et al., "In situ scanning electron microscopy.", Science and Technology of Welding and Joining, vol. 16, Issue 1, pp. 68-78, 2011 (12 pages).

Van Petegem, S et al., "A Miniaturized Biaxial Deformation Rig for in Situ Mechanical Testing.", Experimental Mechanics, vol. 57, Issue 4, pp. 569-580, 2017 (12 pages).

Wilkinson, A.J et al., "High-resolution elastic strain measurement from electron backscatter diffraction patterns: New levels of sensitivity.", Ultamicroscopy, vol. 106, Issues 4-5, pp. 307-313, 2006 (7 pages).

Williams, B.W. et al., "Characterization of anisotropic yield surfaces for titanium sheet using hydrostatic bulging with elliptical dies.", International Journal of Mechanical Sciences, vol. 114, pp. 315-329, 2016 (15 pages).

Zaefferer, S et al., "Theory and application of electron channelling contrast imaging under controlled diffraction conditions.", Acta Materialia, vol. 75, Issue 154, pp. 20-50, 2014 (31 pages).

* cited by examiner

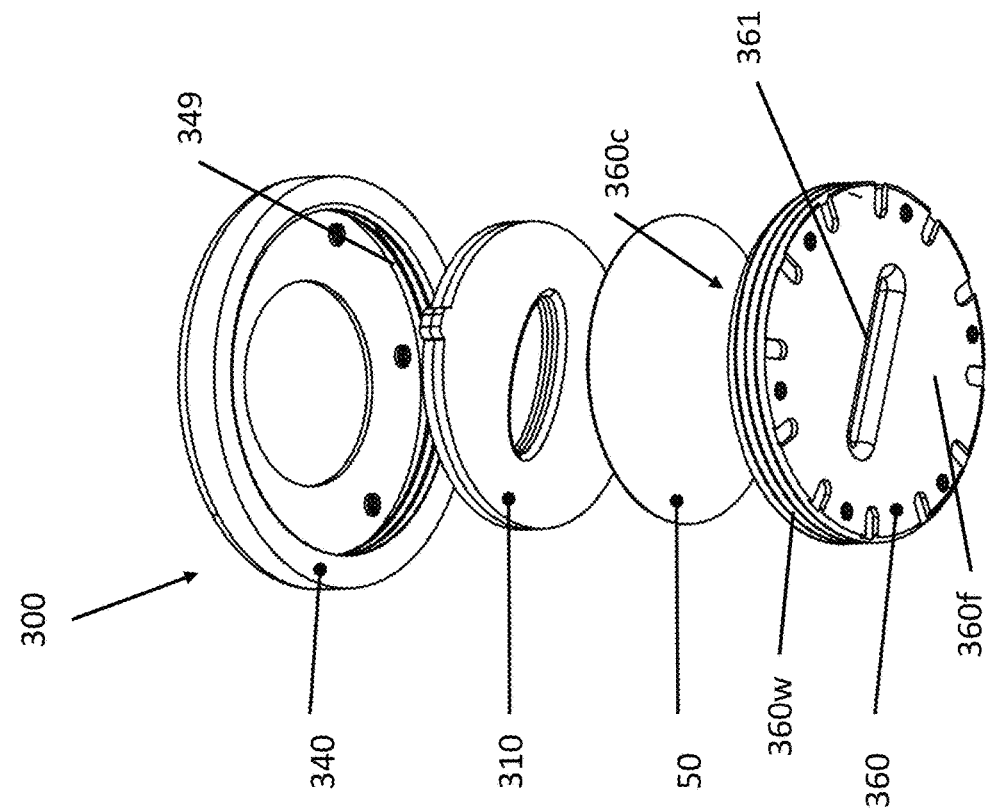
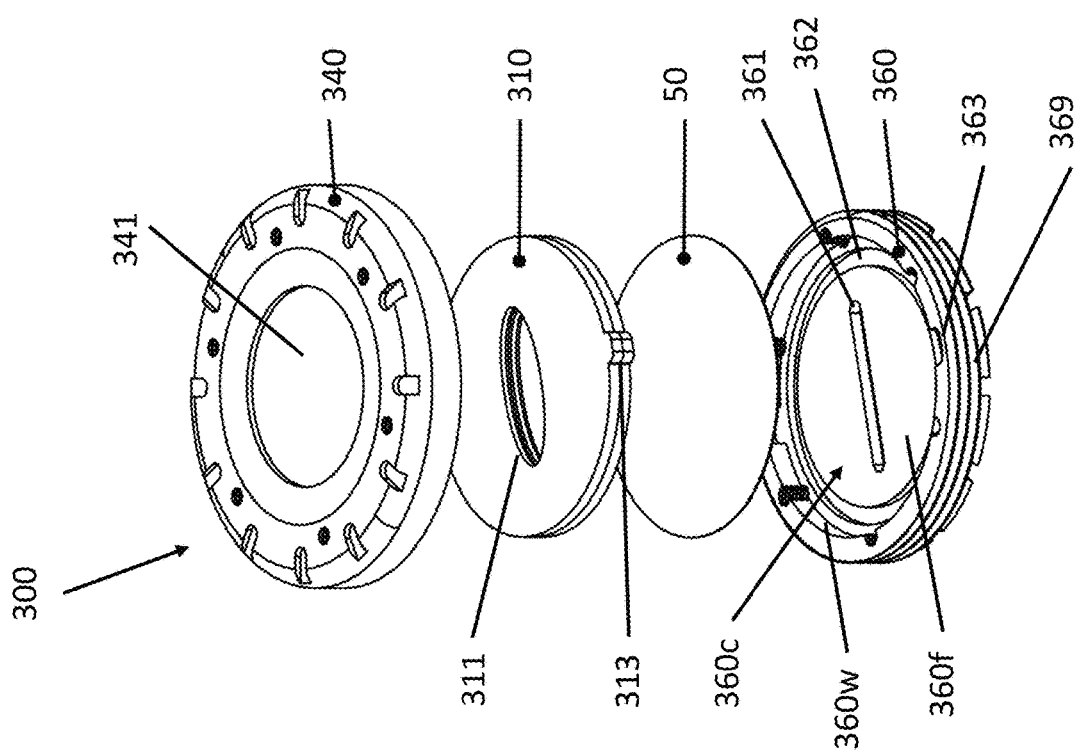
FIG. 3B
FIG. 3A

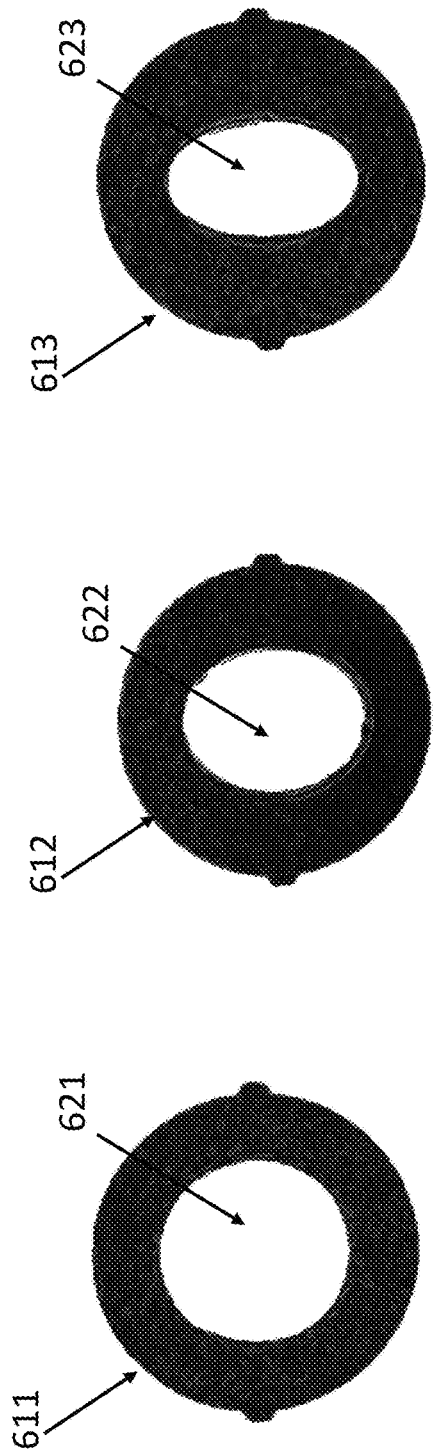
FIG. 5C
FIG. 5B
FIG. 5A
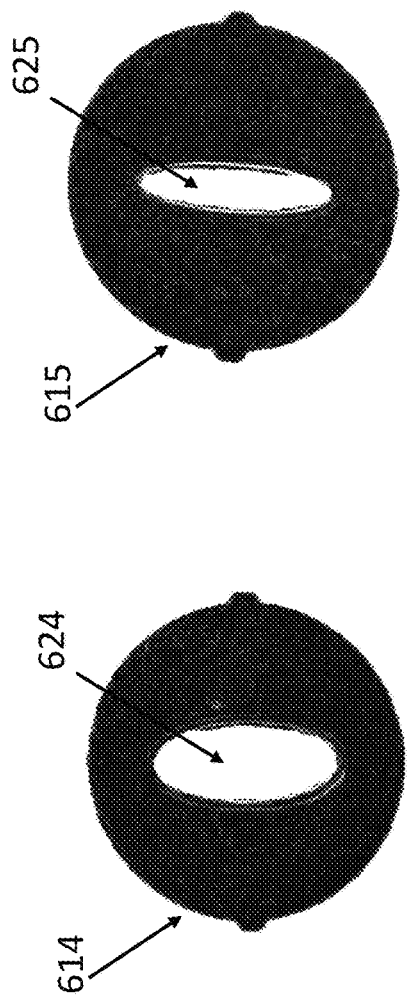
FIG. 5E
FIG. 5D

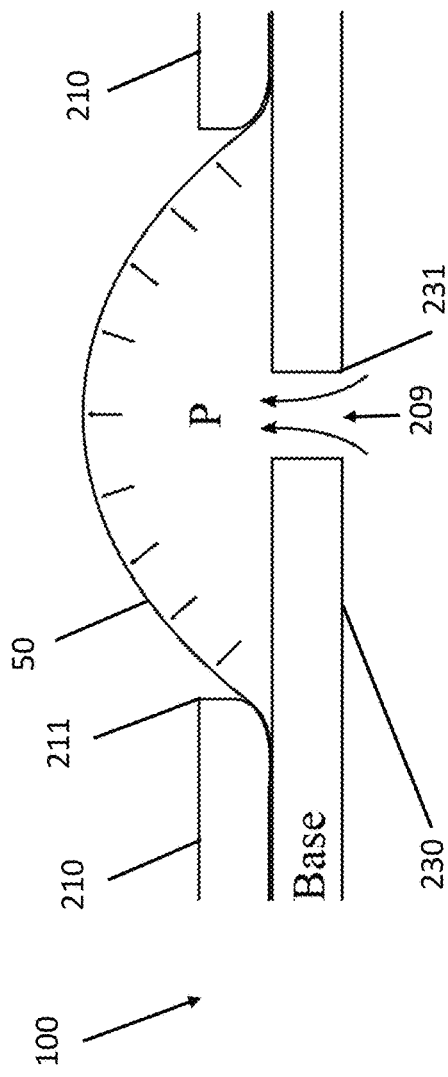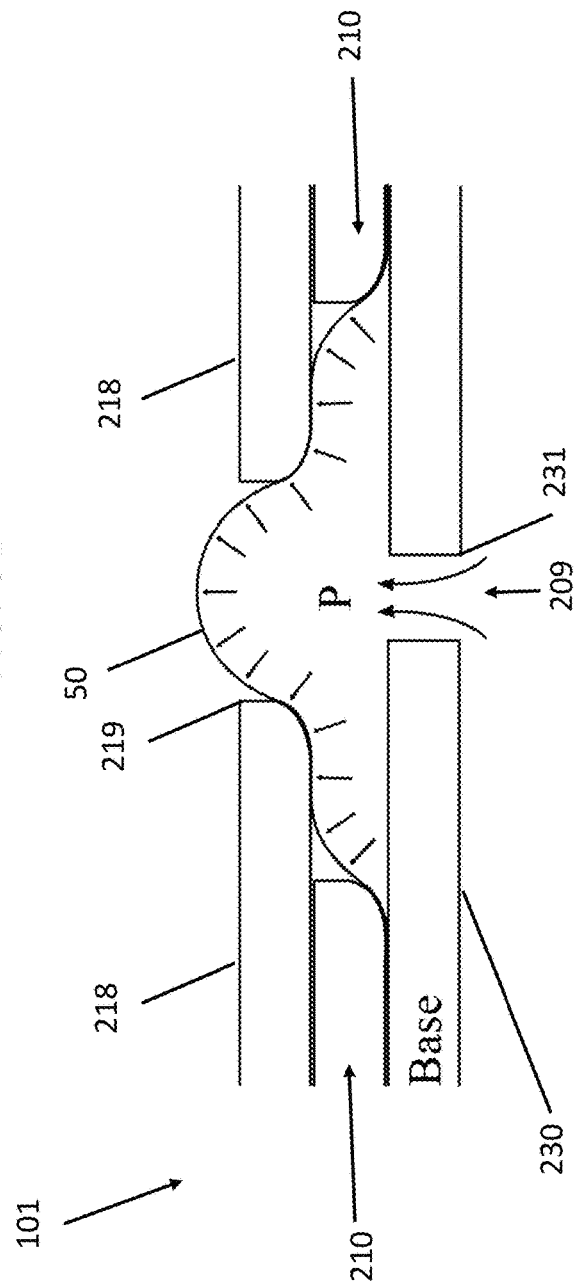

DEVICES AND METHODS FOR HOLDING A SAMPLE FOR MULTI-AXIAL TESTING

RELATED APPLICATIONS

This application claims priority to and the benefit of U.S. Provisional Patent Application No. 62/641,961, filed Mar. 12, 2018, and titled "Devices and Methods for Holding a Sample for Multi-Axial Testing," the contents of which is incorporated herein by reference in its entirety.

FIELD

The present disclosure relates to devices and methods for holding a sample while performing various tests, and more specifically relates to devices and methods that can be used for holding samples in-situ, such as during bulge testing, to allow for multi-axial deformation testing of materials such as metals while allowing for concurrent microstructural observations of the material being tested to be made.

BACKGROUND

What limits the processing limits and service lifetime of structural metals such as FE-, Ti-, Co-, Ni-, and Al-based alloys is nucleation, growth, and coalescence of microstructural damage. In such alloys, damage nucleates as a result of strain incompatibilities and stress concentration between present phases. For a given microstructure, damage mechanisms can vary with local loading conditions and have a direct influence on macroscopic properties such as necking and failure. For example, as damage accumulation takes place before localization, it can significantly impact the forming limit curves (FLC). An improved understanding of the plasticity and damage micro-mechanisms is thus critical in the search for better alloys for numerous structural applications. Moreover, a better understanding of the link between local strain paths and damage mechanisms would shade light on tangled phenomena such as the evolution of FLCs in complex strain paths.

Multiple damage mechanisms can be present in a given alloy. For example, in dual-phase (DP) steels, two mechanisms typically dominate: martensite cracking and martensite-ferrite decohesion. The relative importance of such competing mechanisms can be strongly dependent on local strain paths. In DP steels, a thorough quantitative investigation of damage events in uniaxial, plane strain and biaxial tension has shown that martensite cracking is strongly promoted in biaxial strain states. Quantification of damage incidents can be a tedious task that may require imaging systems with sub-micron spatial resolution, for example, a scanning electron microscope (SEM) or a nano-computed tomography instrument. In situ experiments, coupled with strain mapping techniques, can be an efficient way to track and tally damage events in different strain paths.

Using scanning electron microscopes (SEM), secondary and backscatter electron images can provide statistically relevant data on the location and type of damage events as they can be used to observe large fields of view ($mm^2$) with high spatial resolution (<50 nm). With in situ deformation experiments, mesoscale loading conditions can be measured with digital image correlation (DIC). The DIC technique also can provide a quantitative evaluation of strain localization at the microstructure scale. To benefit from the imaging capabilities of SEMs, a variety of in situ deformation stages have been developed to enable the collection of SE and BSE images at the surface of macro-samples in several strain paths, for example, uniaxial tension, biaxial tension, and shear deformation.

Image-based analyses can provide valuable understanding on the interplay between strain fields and the morphology of the microstructure. Simple morphology-based models can predict trends such as where damage is preferentially nucleated (e.g., in narrow ferrite channels in DP steel) or how some loading conditions influence damage initiation (e.g., martensite cracking can be promoted in biaxial strain paths because of increased notch effects in irregular-shaped martensite islands). To explain the scatter in damage density observed locally, such models need to integrate the role of microstructural features such as boundary types, orientation distributions, and defect densities. Those features cannot be measured through conventional SE or back-scatter detector (BSE) images, but can be accessible with SEM-based analytical techniques.

Electron backscatter diffraction (EBSD) and electron channeling contrast imaging (ECCI) can be used in the SEM to obtain quantitative information on the microstructure such as orientation and phase distributions, boundaries, and local defect densities. The EBSD technique can provide valuable insights into plastic strain fields (with kernel average misorientation (KAM) approaches and geometrically necessary dislocation GND density estimations) and intragranular elastic strain fields. Moreover, EBSD and ECCI can be well suited to investigate plasticity at the dislocation scale. When applied in situ during deformation experiments, the two techniques can be used to track microstructural evolutions and balance them against local strain fields. For example, in situ EBSD can be used to discuss interactions between crack propagation and microstructural features in an austenitic stainless steel. In DP steel, both techniques can be coupled on a deformed sample to investigate the impact of grain and interphase boundaries on the triggering mechanisms of micro-damage features.

One challenge in using multiple techniques consecutively at each step is to find a sample geometry and a loading setup that can fulfill the geometrical requirements of each technique, for example, imaging at a high tilt angle for EBSD or at short working distances for ECCI. In uniaxial tension, several commercial machines designed to pull on flat tensile samples can allow imaging and EBSD. Tilting clamps can be used to reach approximately a 70° tilt, but in some cases the whole stage can be inclined with the microscope stage if the EBSD camera is placed low enough in the chamber (with the sample at an inconvenient working distance of approximately 30 millimeters). To investigate biaxial strain paths, cruciform sample geometries can be employed but, because of the geometrical requirements associated with conventional EBSD, concessions typically have to be made. When using in situ machines with two independent loading axes, degraded EBSD conditions can be met with typically low tilt angles, for example, about 58°. A miniaturized clamp can fit fully tilted under the pole piece and converts a uniaxial load into an equi-biaxial one. In this configuration, quality in situ EBSD can be performed on cruciform samples to study plasticity mechanisms. One additional limitation to the use of cruciform samples for damage monitoring is that the deformation can be intentionally localized by thinning the sample at the center. In that sense, the point of failure can be strongly dependent on the sample geometry and lightly dependent on local microstructure characteristics, for example, texture, phase distribution, and morphology. It can then be questionable whether the damage and failure mechanisms observed are fully representative of the ones activated in sheet forming operations. It appears then that no fully satisfactory solution is available to study damage mechanisms with SEM analytical techniques in situ, especially along bi-axial and complex (non-proportional) strain paths. This is surprising given that, strain paths can strongly influence the nature and distribution of damage mechanisms, contributing to the evolution of forming limit curves.

Accordingly, there exists is a need for in situ deformation experiments involving analytical and imaging techniques to fully understand and characterize the origin and growth of local damage in metallic alloys.

SUMMARY

To improve the understanding of the mechanical behavior of advanced metastable alloys, it is helpful to measure, in a coupled, local, and site-specific manner, evolving mechanical and microstructural fields. Analytical tools and imaging techniques available in a scanning electron microscope readily enable such multi-field mapping approaches during simple mechanical tests. However, when more complex loading scenarios are considered, for example involving multi-axial testing or complex strain paths, more dedicated approaches are required. Certain aspects of the present disclosure provide for a new method to track site-specific microstructure evolution in metals deformed multi-axially along proportional or complex strain paths. Certain example methods employ a custom-designed miniaturized bulge-test setup featuring a removable sample holder which enables analytical measurements in a scanning electron microscope.

As described herein, SEM-based analytical techniques can be used to study damage mechanisms in samples deformed along biaxial and complex strain paths. Certain aspects of the present disclosure provide for a miniaturized bulge test that uses a sample holder in combination with elliptical dies, and a method to impose strain path changes during such testing. The circular bulge test is an established method to study the equi-biaxial response of sheet metal in tension (ISO 16808 2014). Coupled with optical measuring systems, it can be a convenient way to obtain equi-biaxial stress-strain curves and can be a key tool to study yield surfaces. Compared to other biaxial testing methods such as punch-based tests, insights into local stress states can be easily available as the surface of bulge test samples are typically loaded without friction. The knowledge of local stress state can be extremely useful to investigate local events such as the effect of stress triaxiality on damage nucleation in DP steel. The method can be used for sheet metal testing. The technique is also widely used also to investigate the mechanical response of thin films and biological tissues. The present disclosure provides for bulge test apparatuses having elliptical dies (i.e., washers), which can be used to investigate a large portion of the tension-tension side of forming limit diagrams, among other uses provided for herein or otherwise known to those skilled in the art in view of the present disclosures. The devices of the present disclosure can be designed to generate complex strain paths at the center of a sample, therefore in situ-like observations in the SEM can provide valuable input data for microstructure-based simulations used to capture the hardening of samples along complex strain paths.

Samples prepared from both commercial sheet metal (dual-phase steel) and foils (stainless steel) were tested as validation experiments. Strain measurements with the digital image correlation technique confirmed that both proportional strain paths and complex strain paths can be investigated with this method, while electron backscatter diffraction (EBSD) and electron channeling contrast imaging (ECCI) analyses demonstrated the possibility to monitor local crystal plasticity and dislocation activity. The approach is versatile, and has the potential to enable a wide range of investigations regarding strain path effects on plasticity and damage.

Many configurations of devices and methods are made possible by aspects of the present disclosure. Some non-limiting, exemplary embodiments of devices and methods are summarized and claimed below. It is noted that to the extent the present disclosure discusses DP steel, a person skilled in the art, in view of the present disclosures, will understand DP steel is merely one, non-limiting example of a metallic structure that can be used in accordance with disclosures provided for herein. Other metals, alloys, and the like can likewise be used in conjunction with the present teachings related to testing devices and methods without departing from the spirit of the present disclosure.

Embodiments include incremental EBSD and ECCI conducted in configurations relevant for multi-scale investigations of localized plasticity and damage mechanisms in different materials. Aspects can enable multi-field mapping strategies to characterize fundamental mechanisms activated in biaxial and complex loadings. Incremental ECCI and EBSD observations during bulge experiments can provide valuable insights into the mechanisms of strain localization and damage nucleation in DP steels. Strain paths have a key impact on damage events and the formability of sheet metal. In some embodiments, SEM-based techniques are used to provide quantitative and qualitative data on localized plasticity and damage at different length scale in the microstructure. Incremental ECCI can be used to track dislocation activity at early stages of plasticity, in a configuration relevant to investigate mechanisms activated in the elasto-plastic transition or in fatigue loadings. EBSD-based quantitative analyses such as kernel average misorientation (KAM) approaches can be used to characterize strain localization around a defect in a configuration usually employed to study damage nucleation.

The ability to track dislocations in biaxial strain paths with incremental ECCI opens up new perspectives, for example, regarding the investigation of continuous yielding. Dislocation slip at early deformation levels can be evaluated in specific locations such as the vicinity of martensite islands by selecting them using the large field of view of the SEM. In this manner, dislocation activity can be correlated to intragranular elastic strain stemming from the martensitic phase transformation by using an initial high angular resolution EBSD measurement on the flat sample. ECCI under controlled channeling conditions can be performed with the aspects of the present disclosure by, for example, using an EBSD orientation measurement to control channeling conditions.

The ability to perform incremental EBSD with aspects of the bulge test approach using the methods and systems disclosed herein gives access to a quantitative evaluation of microstructural evolutions otherwise difficult to obtain in biaxial strain paths. Orientation imaging can provide valuable data on the role of microstructural features (slip systems activated, type of boundaries, etc.) and quantitative indices on some mechanical fields (plastic strains, GNDs, etc.) that could be correlated, for example, to damage initiation mechanisms.

In some instances, a benefit of the SEM-based observations the bulge test approaches provided by aspects of the present disclosure is to enable multi-scale measurements to be performed down to the dislocation scale. Aspects of the present disclosure enabled multiple techniques, for example, DIC and EBSD, to be coupled together to investigate mechanisms activated in biaxial loadings along proportional and complex strain paths.

Certain aspects of the present disclosure are targeted to improve current techniques in which a microstructure of a metallic structure is evaluated using a combination of known strength and strain tests and looking at the metallic structure (or some portion thereof) under a microscope, such as an SEM. Prior techniques were limited in their abilities to assess complex strain paths, often requiring a number of deformation steps be performed to achieve a desired bend in the metal being evaluated. The present disclosure, however, allows for deformation to occur by way of a complex strain path while testing is being performed. Further, the present disclosure allows for many different types of tests to be performed because certain aspects of the present disclosure can be used with a variety of different types of scientific instruments, for example, microscopes, including microscopes those having skill in the art know to be sophisticated, RX diffraction instruments.

The teachings of the present disclosure can be used in a variety of different contexts and across a variety of industries. By way of non-limiting example, the present disclosures can be applied to deform and test sheet metal that is used in bigger structures, such as cars, planes, and in other factories. Using existing techniques, it can be difficult to analyze the sheet metal once multiple bends are made in it. As metal get thicker, it takes more time to shape it, so the formation of such metals can be time-intensive. Certain aspects of the present disclosure alleviates those problems. In some instances, sheet metal that can be used in conjunction with the present disclosures can have a thickness approximately in the range of about 0.01 millimeter to about 1 millimeter, and in some embodiments the thickness can be about 0.1 millimeter, although a person skilled in the art will recognize other thicknesses smaller or larger than those indicated can also be used in conjunction with the present disclosures. By way of further non-limiting example, the present disclosures can be applied to foils, such as those used in various electronics. The present disclosures allow for such foils to be shaped as desired while also performing desired tests on or to the foils.

One common, but non-limiting example of a test that can be performed in conjunction with the present disclosures is a bulge test. The bulge test can be used in conjunction with sheet metal and foils, among many other types of metal components. The present disclosure revolutionizes bulge testing, however, because it allows for the testing to be done in a miniaturized, compact, and convenient manner that was not possible with bulge testing prior to the present innovations. Prior to the present innovation, bulge testing used bulky parts, did not allow for samples being tested to be easily viewed during the testing process (typically only from above the testing apparatus and/or from far away), and was not generally transportable between various testing apparatuses, such as microscopes, to allow for different types of tests with different types of equipment. Further, the present disclosure provides for a clamping component or instrument to be separate from a pressure system used during bulge testing, which is different than existing bulge testing set-ups in which the clamping instrument and pressure system were combined.

In one exemplary embodiment of a device for holding a sample, the device includes a base, a cover, and one or more washers configured to be disposed between the base and the cover when the base and the cover are coupled together. The base has a floor and one or more walls that extend above the floor to form a receiving chamber for receiving a sample. Further, the floor has one or more apertures extending through the floor for receiving a pressure-supplying fluid. The cover has a configuration that is complementary to at least a portion of the base such that the cover and base can be coupled together to tightly clamp a sample disposed in the receiving chamber. The cover has an opening that extends through it. Each washer of the one or more washers has one or more openings that extend through the washer. The one or more openings are configured to change at least one of a shape and a size of the opening formed in the cover. Although terms such as device, base, cover, and washer, are used herein, a person skilled in the art will recognize other terms can also be used either because they are provided for herein or are otherwise understood in the art in view of the present disclosure. For instance, a device may also be referred to as an apparatus or system, among other terms, and a washer may be referred to as an adjustment mechanism, die, adjuster, or configuration plate at least because the purpose of the one or more washers is to adjust or reconfigure a shape of the opening formed in the cover. Other terms for the device, washer, base, and cover are also possible.

In some embodiments, the device can also include one or more seals that are associated with the base. The seals can be configured to prevent device leakage when a pressure-supplying fluid is supplied to the base via the one or more apertures of the base. The one or more seals can be considered to be a sealing system of the device. In some instances, at least one of the seals includes an o-ring. The device can be configured to be separately mounted from a pressure system that is configured to apply a pressure-receiving fluid to the base via the one or more apertures of the base.

The cover can be substantially transparent to allow for observation of a sample disposed in the receiving chamber when a pressure-supplying fluid is being applied to the one or more apertures of the base. The pressure can be supplied by a pressure chamber, such as is done when performing tests like a bulge test. An observation angle of the device when the cover is coupled to the base to tightly clamp a sample disposed in the receiving chamber can be approximately 70 degrees or less. The observation angle can be viewed from a location that is approximately in the range of about one (1) millimeter to about ten (10) millimeters from a closest position of a perimeter of the device. In some such instances, the observation angle can be viewed from a location that is approximately five (5) millimeters from the closest portion of the perimeter of the device. A person skilled in the art will understand that other viewing distances are possible, including distances less than one (1) millimeter and greater than ten (10) millimeters.

The devices of the present disclosure can be considered to be miniature in nature as compared to existing holding devices for tests like bulge testing and in situ testing. For example, a height of the device when the cover is coupled to the base to tightly clamp a sample disposed in the receiving chamber can be approximately five (5) millimeters or less. Likewise, a diameter of the device when the cover is coupled to the base to tightly clamp a sample disposed in the receiving chamber can be approximately 32 millimeters or less.

The one or more washers can include a plurality of washers. In some such instances, the one or more openings of a first washer of the plurality of washers and the one or more openings of a second washer of the plurality of washers can be configured to be rotated with respect to each other to provide multiple shapes and/or multiple sizes of the opening formed in the cover. Alternatively, or additionally, the one or more openings of a first washer of the plurality of washers and the one or more openings of a second washer of the plurality of washers can have an elliptical ratio that is different than 1:1. Still further alternatively, or further additionally, a first washer of the plurality of washers and a second washer of the plurality of washers can have an elliptical ratio that is different than 1:1. The plurality of washers in any instance can be configured to create one or more complex strain paths for a sample disposed in the receiving chamber. Additionally, or alternatively, the one or more openings of the plurality of washers can be substantially elliptical in shape, with an opening of the one or more openings of a first washer of the plurality of washers can have a different elliptical size and/or shape than an opening of the one or more openings of a second washer of the plurality of washers. The one or more washers in any instance can include one or more clamping ends that extend radially outward from a main body of the one or more washers. The one or more clamping ends can be configured to engage one or more complementary receiving ends disposed in the base and/or the cover.

A shape of the base and a shape of the cover can be approximately elliptical. In some such instances, the shape of the base and the shape of the cover can be approximately circular. The base can be configured to be mounted to a scanning electron microscope, among a host of other testing apparatuses, viewing instruments, etc. with which the device can be used.

In one exemplary embodiment of a kit, the kit includes one or more bases, one or more covers, and a plurality of washers. Similar to as mentioned above, other terms in lieu of terms like kit, base, cover, and washer can be used without departing from the spirit of the present disclosure, such as alternative terms for the term "washer." Each base of the one or more bases includes a floor and one or more walls that extend above the floor to form a receiving chamber for receiving a sample. Further, the floor has one or more apertures extending through the floor for receiving a pressure-supplying fluid. Each cover of the one or more covers has a configuration that is complementary to at least a portion of the one or more bases such that the cover and the one or more bases can be coupled together to tightly clamp a sample disposed in the receiving chamber. The cover has an opening that extends through it. Each washer of the plurality washers has one or more openings that extend through the washer. The one or more openings are configured to create one or more complex strain paths for a sample disposed in the receiving chamber by changing a shape and/or size of the opening formed in the cover.

In some embodiments, the kit can also include a plurality of seals that are configured to be associated with the one or more bases. Each seal of the plurality of seals can be configured to prevent device leakage when a pressure-supplying fluid is supplied to the base via the one or more apertures of the base. A single seal can be used per device, or multiple seals can be used in one device. The seal(s) can be considered to be a sealing system of the device. In some instances, at least one of the seals includes an o-ring. The device(s) that results from the kit can be configured to be separately mounted from a pressure system that is configured to apply a pressure-receiving fluid to the base via the one or more apertures of the base.

At least one cover of the one or more covers can be substantially transparent to allow for observation of a sample disposed in the receiving chamber of the one or more bases when a pressure-supplying fluid is being applied to the one or more apertures of the one or more bases. The pressure can be supplied by a pressure chamber, such as is done when performing tests like a bulge test. An observation angle of a device resulting from coupling a base of the one or more bases and a cover of the one or more covers to tightly clamp a sample disposed in the receiving chamber of the base can be approximately 70 degrees or less. The observation angle can be viewed from a location that is approximately in the range of about one (1) millimeter to about ten (10) millimeters from a closest position of a perimeter of the device resulting from coupling the base to the cover. In some such instances, the observation angle can be viewed from a location that is approximately five (5) millimeters from the closest portion of the perimeter of the device resulting from coupling the base to the cover. A person skilled in the art will understand that other viewing distances are possible, including distances less than one (1) millimeter and greater than ten (10) millimeters.

The components of the kit of the present disclosure, and thus the devices that result from combining components of the kit together, can be considered to be miniature in nature as compared to existing components for holding devices for tests like bulge testing and in situ testing. For example, a combined height of a base of the one or more bases and a cover of the one or more covers when coupled together to tightly clamp a sample disposed in the receiving chamber of the base can be approximately five (5) millimeters or less. Likewise, a diameter of the one or more covers, or of the resulting device when a cover of the one or more covers is coupled to a base of the one or more bases to tightly clamp a sample disposed in the receiving chamber of the respective base can be approximately 32 millimeters or less.

Each washer of the plurality of washers can be configured to be rotated with respect to another washer of the plurality of washers to provide multiple shapes and/or multiple sizes of the opening formed in the cover. Alternatively, or additionally, the one or more openings of a first washer of the plurality of washers and the one or more openings of a second washer of the plurality of washers can have an elliptical ratio that is different than 1:1. Still further alternatively, or further additionally, a first washer of the plurality of washers and a second washer of the plurality of washers can have an elliptical ratio that is different than 1:1. Additionally, or alternatively, the one or more openings of the plurality of washers can be substantially elliptical in shape, with an opening of the one or more openings of a first washer of the plurality of washers can have a different elliptical size and/or shape than an opening of the one or more openings of a second washer of the plurality of washers. Each washer of the plurality of washers can include one or more clamping ends that extend radially outward from a main body of the respective washer. The one or more clamping ends can be configured to engage one or more complementary receiving ends disposed in the base and/or the cover.

A shape of the one or more bases and a shape of the one or more covers can be approximately elliptical. In some such instances, the shape of the one or more bases and the shape of the one or more covers can be approximately circular. The one or more bases can be configured to be mounted to a scanning electron microscope, among a host of other testing apparatuses, viewing instruments, etc. with which the device resulting from resulting from coupling the a base of the one or more bases to a cover of the one or more covers.

One exemplary method of analyzing a metallic structure includes disposing a metallic structure in a holder, coupling the holder to a testing apparatus, and applying a fluid pressure from a fluid pressure system to the holder, which causes the metallic structure disposed in the holder to deform in a manner prescribed by a configuration of the holder. The method further includes observing features of the metallic structure by looking through a side surface of the holder. The fluid pressure system is separately disposed from each of the holder and the testing apparatus such that each can be disassociated from the other for use elsewhere.

In some embodiments, the method further includes decoupling the holder from the testing apparatus. In some such embodiments, the metallic structure can be removed from the holder and a second metallic structure can be disposed in the holder. The holder can then be coupled to the testing apparatus, a fluid pressure can be applied from the fluid pressure system to the holder to cause the second metallic structure disposed in the holder to deform in a manner prescribed by a configuration of the holder, and observing features of the second metallic structure by looking through a side surface of the holder. Alternatively, after the second metallic structure is disposed in the holder, the holder can be coupled to a second testing apparatus, and the second testing apparatus can be operated to effect the second metallic structure. In yet some other embodiments, after decoupling the holder from the testing apparatus, the holder can be coupled to a second testing apparatus, with the second testing apparatus being operated to effect the second metallic structure.

Some of the methods provided for herein can include selecting at least one washer and disposing the selected washer(s) in the holder to derive a desired configuration of the holder. The desired configuration of the holder can be configured to achieve a desired metallic structure deformation. The selected washer(s) can be rotated with respect to the holder. Thus, in some instances, the method can include rotating one or more washers disposed in the holder with respect to the holder to adjust the configuration of the holder. This can also result in changing the way in which the metallic structure deforms. In some such embodiments, rotating one or more washers disposed in the holder with respect to the holder can include rotating a first washer with respect to a second washer to adjust the configuration of the holder, thus changing the way in which the metallic structure deforms.

A person skilled in the art will recognize a number of other devices, kits, and methods that can be derived from the disclosures provided for herein.

BRIEF DESCRIPTION OF DRAWINGS

This disclosure will be more fully understood from the following detailed description taken in conjunction with the accompanying drawings, in which:

FIG. 3A is an exploded top perspective view of the sample holding device of FIG. 2A;

FIG. 3B is an exploded bottom perspective view of the sample holding device of FIG. 2A;

FIGS. 5A-5E are top views of washers for use in conjunction with a sample holding device, each washer having an opening of different ellipticity.

FIG. 6E is a cross-sectional view similar to the view of FIG. 6C, although a configuration of the washer and the base is different than the configuration shown in FIG. 6C, yielding a different deformation of the material sample during a bulge deformation test; and FIG. 6F is a cross-sectional view similar to the view of FIG. 6C, although a second washer is also included such that a configuration of the washer, the second washer, and the base is different than the configurations shown in FIGS. 6C and 6E, yielding a different deformation of the material sample during a bulge deformation test.

DETAILED DESCRIPTION

Figure 1A:
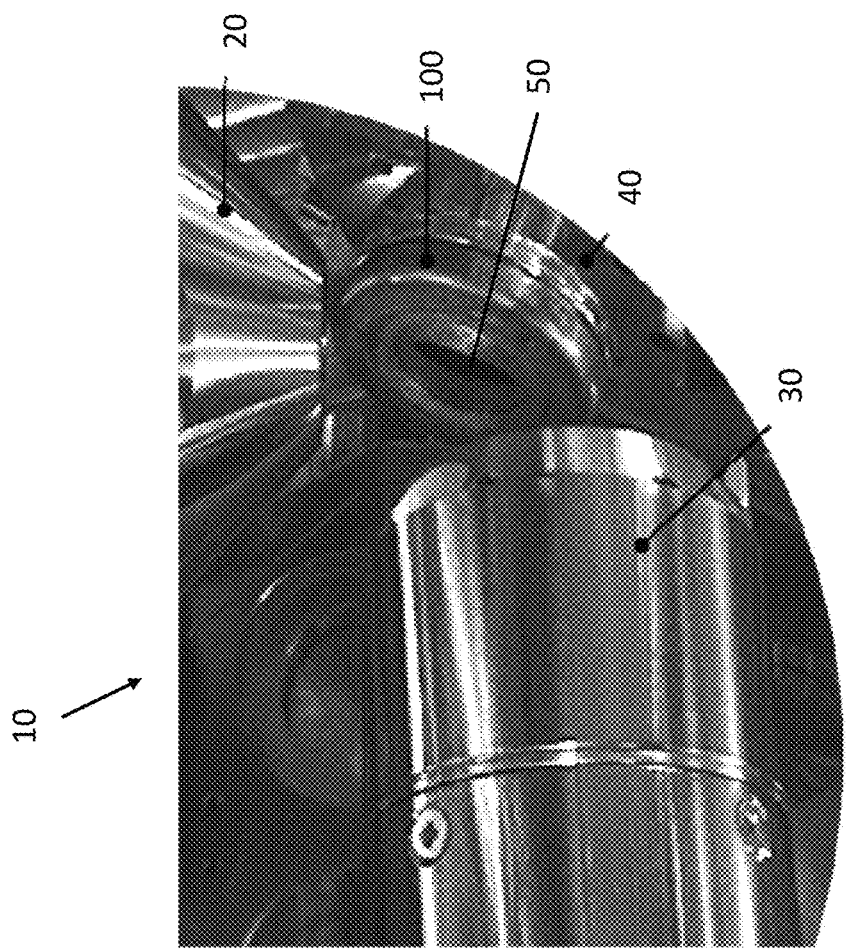
FIG. 1A is a perspective view of one exemplary system arranged to deform samples in biaxial strain paths while EBSD is carried out.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

To the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape. Sizes and shapes of the devices and systems, and the components thereof, can depend, at least in part, on the intended use of the devices and systems, and the sizes and shapes of other devices, systems, and the like with which the disclosed devices and systems are used.

One of the challenges in the design of structural alloys is to achieve optimal combinations of strength, toughness, and ductility. The general trend to overcome this challenge is to design metals with complex microstructures containing multiple phases with contrasted mechanical properties. Examples are numerous: dual phase steels, duplex stainless steels, α+β titanium alloys, nickel-based superalloys, cobalt alloys, etc. These alloys can be engineered to have a wide range of microstructure characteristics (e.g., phase volume fractions, morphologies, sizes, and distributions), creating a vast spectrum for microstructure design. However, the assembly of contrasted phases leads, during deformation, to microscale stress-strain localization and damage phenomena that depends, at least in part, on the local stress state, the strain path followed, and the presence of strain path changes. As microstructural damage often leads to premature necking or failure at the macro-scale, those phenomena are of specific importance for the sheet metal forming and automotive industries. There is thus a great interest to develop experimental methods that would allow linking complex loading conditions to simultaneous measurements of mechanical and microstructural fields (i.e., multi-field mapping), with the goal to shed light on the link between plasticity, damage mechanisms, and microstructure characteristics. To this end, experimental considerations worth considering include: (i) having a tool with a range of analytical techniques that combine mapping capabilities with high spatial resolution to capture, for example, damage nucleation processes, and large field-of-view to capture long-range 'neighborhood' effects; and (ii) using the proper deformation stage to impose mechanical boundary conditions on the sample in a controlled manner.

Regarding the first challenge, scanning electron microscopes (SEM) can enable measurements with both high spatial resolution (<~10 nm) and large field-of-view (~$mm^2$). Analytical SEM techniques, such as electron backscatter diffraction (EBSD) and electron channeling contrast imaging (ECCI), provide valuable new insights into local defect evolution, plastic strain fields, intragranular elastic strain fields, boundary damage mechanisms, and microcrack microstructure interactions. Employing digital image correlation (DIC) on SEM images, quantitative evaluation of microscopic strains can be measured, most accurately by employing submicron-sized artificial patterns. Coupling DIC and absolute HR-EBSD can enable direct measurement of the local behavior of the material, for example, using synchrotron techniques. When applied in situ during deformation experiments, EBSD and DIC have been used to track microstructural evolutions and analyze them in connection to local strain fields.

To address the second challenge, a variety of in situ SEM deformation stages have been developed to explore different deformation modes. For example, uniaxial tension, biaxial tension, shear deformation, etc. However, regardless of how miniaturized such setups are, once installed in the SEM chamber, the geometrical requirements of different imaging modes, for example, EBSD, ECCI, or in-lens SE for DIC, become a challenge in a multi-field mapping approach where several techniques have to be employed consecutively. In commercial uniaxial straining stages, EBSD can be performed by employing 70° pre-tilted clamps or tilting the SEM stage. The latter can require specific EBSD camera positions and large working distances. In either case, switching back to, for example, in-lens SE mode (0°) or ECCI mode (<~10°, with a short working distance) are not always practical. The case of biaxial straining can be even more challenging due to the complexity of required deformation setups. For cruciform-type geometries with two independent loading axes, low tilt angles are typically employed for EBSD measurements, for example, ~58°. An alternative approach is design a mechanism that imposes an equibiaxial loading from a single loading axis. A miniaturized Marciniak test setup can provide a clean multi-axial deformation state, however, with this setup, in situ EBSD is not possible. Given all these limitations, aspects of the present disclosure provide new methods to track plasticity and damage mechanisms along biaxial and complex (non-proportional) strain paths, while employing various SEM mapping modes.

Certain aspects of the present disclosure enable the use of SEM-based analytical techniques to study plasticity and damage mechanisms in samples deformed along biaxial and complex strain paths. In some instances, this is achieved by introducing a miniaturized bulge test setup with elliptical dies, featuring a sample holder adapted for EBSD/ECCI measurements and a method(s) to impose strain path changes.

The bulge test is a method that can be used to measure biaxial stress-strain curves, yield surfaces, forming limit curves (FLC), or characterize damage mechanisms of sheet metal (as well as the mechanical response of thin films or biological tissues). The use of frictionless boundary conditions enables simple analytical formulae to be used to assess the sample mechanical response. On top of these advantages, aspects of the present disclosure include a bulge test setup with a dedicated sample holder that can also provide: (i) non-proportional, complex, multi-axial strain paths; and (ii) high quality EBSD, ECCI, and DIC measurements. While, in some instances, the loading is carried out ex situ, certain aspects disclosed herein overcome limitations found in interrupted tests, such as unloading or re-clamping effects.

Figure 1B:
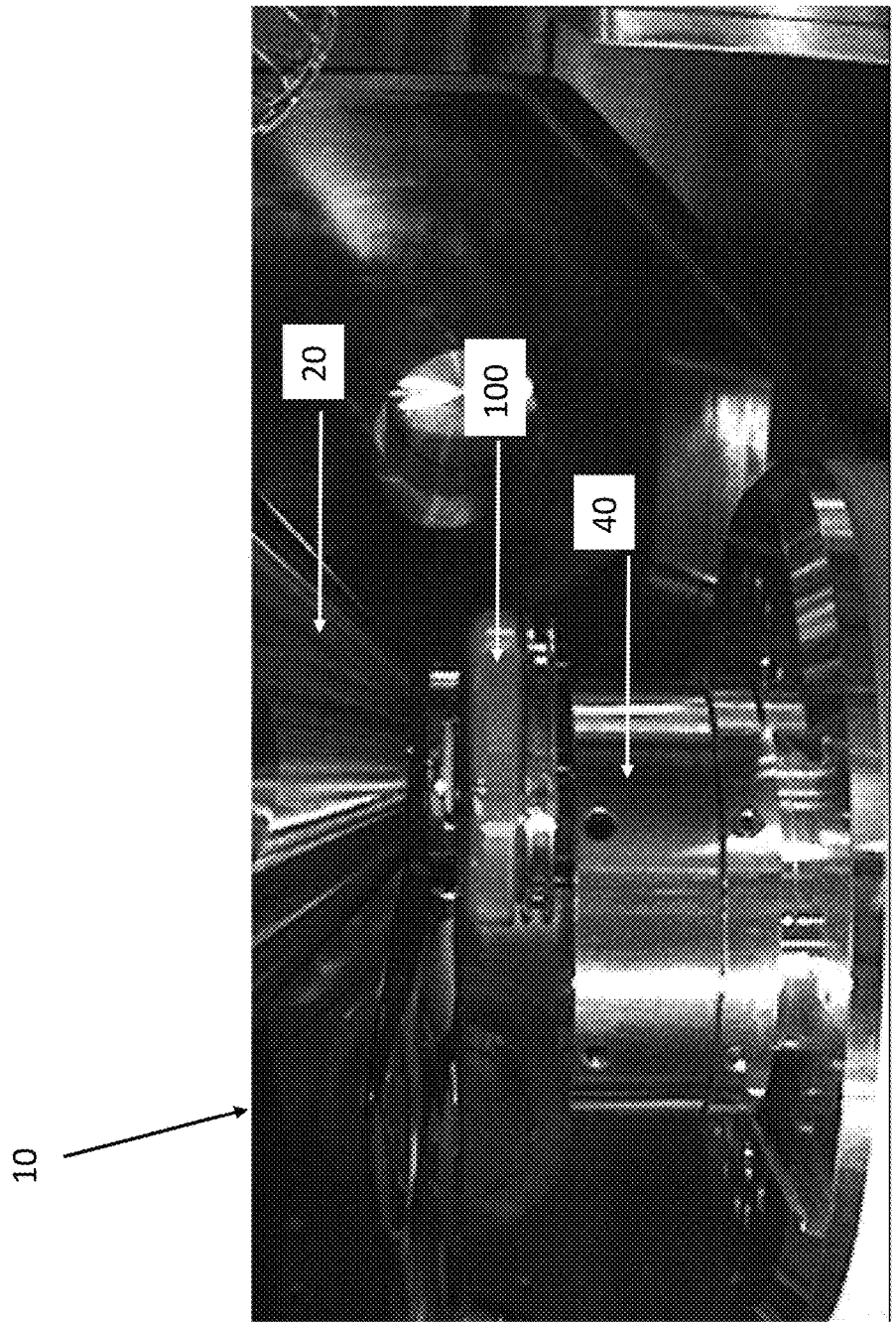
FIG. 1B is side view of the exemplary system of FIG. 1A arranged to perform ECCI.

FIGS. 1A and 1B illustrate an example system arranged to deform thinned dual-phase steel samples and stainless steel foils in biaxial strain paths while ECCI and EBSD were carried out incrementally to investigate microstructural mechanisms. More particularly, FIG. 1A shows the example system arranged to deform samples in biaxial strain paths while electron backscatter diffraction (EBSD) is carried out. The illustration shows a scanning electron microscope (SEM) system 10 including a pole piece of an SEM 20, an EBSD detector 30, a SEM stage 40, and a sample holder 100 containing a material sample 50. The sample holder 100 is positioned on the SEM stage 40 at an angle of approximately 70 degrees with respect to the SEM 20, which positions the sample 50 with respect to the SEM and EBSD detector in order to conduct the EBSD measurement. In some instances, the sample holder 100 is first positioned onto the SEM stage 40 in a flat position, and then the SEM stage 40 is tilted to bring the sample holder 100 to the desired angle (e.g., approximately 70°, as shown) with respect to the horizontal plane of the SEM 20. A person skilled in the art will appreciate that while FIGS. 1A and 1B do not illustrate the entirety of an SEM, a full SEM, and its related setup, are understood by a person skilled in the art, and thus a full illustration of the same is unnecessary.

In a representative example to better understand how devices of this nature operate, a disc-shaped sample 50 with a radius of approximately 12 millimeters and a thickness of approximately 100 μm, is first clamped in a sample holder 100 associated with the SEM system 10, and is then gradually pushed through an elliptical opening of the sample holder 100 with hydraulic pressure (not shown) until the flat sample 50 deforms into a dome with a near elliptical shape. Additional information about the configuration of the sample holder 100 will be discussed in greater detail below. In some instances, the pressure generator is set to deliver a linear increase in pressure with time, using ethanol as hydraulic media. In a non-limiting example experiment, the lowest loading speed available was selected to perform quasi-static tests: for monotonic loadings, the maximum pressure available (230 bar) was reached in approximately 5 minutes. Initial strain rates at the center of the experiment vary with both the thickness of each sample and the dies used but all values measured stayed below $10^{-3}$ s$^{-1}$. Note that the linear increase in pressure generates an exponential-like increase in strain rate as deformation proceeds, and in this example experiment, the highest strain rate measured before failure (with an acquisition rate of 1 Hz) was approximately $6.10^{-3}$ s$^{-1}$.

The design of the sample holder 100 is configured to ensure identical mechanical boundary conditions and consistent imaging conditions during an interrupted test. In operation, the sample holder 100 can be taken to the SEM stage 40 and back to the pressure chamber at any point during the test, without having to unclamp the sample 50 being deformed. Several geometrical constraints have been considered during the design of the sample holder 100 to be able to perform EBSD and ECCI in optimal conditions. By way of non-limiting examples, a ~70° tilt, ~15 millimeters working distance for EBSD, and <~10° tilt, ~7 millimeters working distance for ECCI. The sample holder 100 can be placed on virtually any SEM stage 40 to carry out EBSD measurements at the center of the sample 50, in an optimal position. Conventional imaging (SE/BSE/In-lens) and ECCI observations can also be conveniently performed because switching between different observation techniques is achieved by simply tilting the SEM stage 40.

FIG. 1B illustrates the example SEM system 10 of FIG. 1A arranged to perform ECCI. In FIG. 1B, the SEM stage 40 has moved the sample holder 100 into close proximity with the pole piece of the SEM 20 (e.g., ~7 millimeters) to conduct ECCI of the sample 50.

Figure 2B:
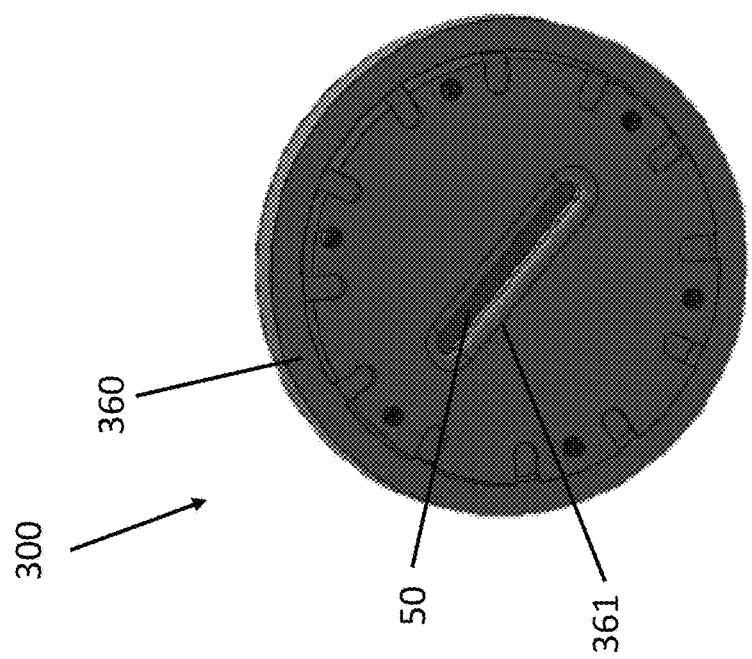
FIG. 2B is a bottom perspective view of the assembled sample holding device of FIG. 2A.
Figure 2A:
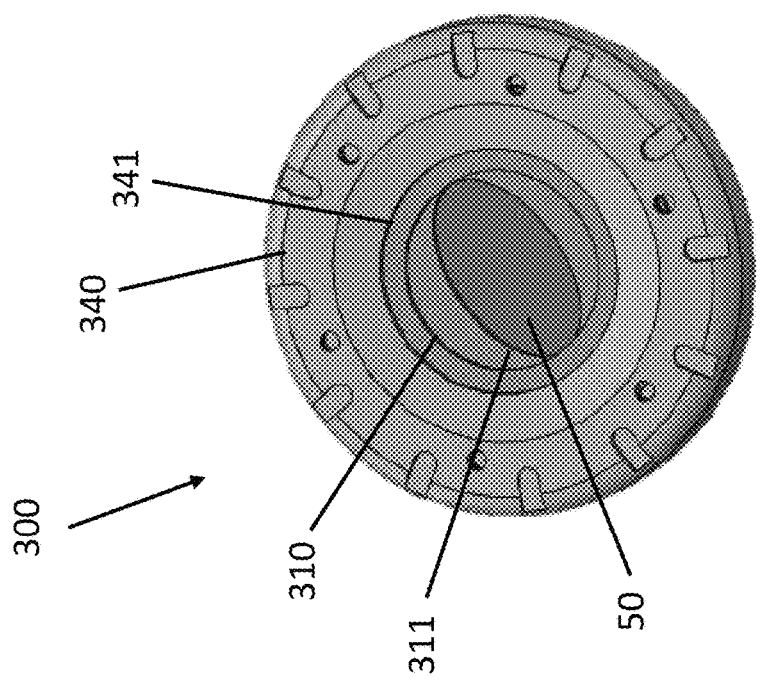
FIG. 2A is a top perspective view of one exemplary embodiment of an assembled sample holding device that includes a washer and a sample of material to be tested.

FIGS. 2A and 2B are illustrations of an assembled sample holding device 300 containing a washer 310 and a sample of material 50 to be tested. The sample holding device 300 can be configured to securely hold the sample 50 in position during hydraulic deformation and subsequent testing. The sample holding device 300 can enable the sample 50 to undergo the hydraulic deformation on a hydraulic pressure apparatus and then be transferred to an SEM or other imaging apparatus for investigation. The sample holding device 300 thereby can provide a portable rig for deforming and investigating material samples 50 without decoupling the sample 50 from the deformation surfaces, such as a washer 310.

FIG. 2A shows the sample holding device 300 can include a cover 340 that can surround a washer 310. The cover 340 can include an opening 341 through which the washer 310 is visible. In some embodiments, the cover 340 itself can be substantially transparent. The washer 310 includes an opening 311 through which the sample 50 can be visible. The opening 311 of the washer 310 can be configured in a manner such that it changes at least one of a shape and a size of the opening 341 of the cover 340, as illustrated in greater detail below. The cover 340 can surround the washer 310 and the sample 50 and can hold them between the cover 340 and a base 360, as shown in FIG. 2B. The base can include a floor 360$f$ and one or more walls, as shown a cylindrically shaped wall 360$w$, that extends above the floor 360$f$ to form a receiving chamber 360$c$ for receiving the sample 50. The base 360 can cover the back of the sample 50 and can be secured to the cover 340 around the periphery of the washer 310 using any technique known for coupling two components together. The base 360 includes one or more openings or apertures 361 to permit the delivery of a pressure-supplying fluid, such as a hydraulic fluid, to the back side of the sample 50. The base 360 can be configured to be mounted to an SEM and/or other devices. Alternatively, or additionally, the sample holding device 300 itself, for instance via the base 360, can be configured to be separately mounted from a pressure system that is configured to apply a pressure-receiving fluid to the aperture 361.

The cover 340 and the base 360 can have complementary configurations such that the cover 340 and base 360 can be coupled together to tightly clamp the sample 50 disposed in the receiving chamber 360$c$. In instances where the cover is substantially transparent, it allows for observation of the sample 50 disposed in the receiving chamber 360 when a pressure-supplying fluid is being applied via the aperture 361.

The sample holding device 300 can be configured to enable multi-axial deformation of metallic foils, such as a miniaturized bulge test, with concurrent microstructural observation, for example, in a scanning electron microscope. The cover 340 and base 360 of the sample holding device 300 can tightly clamp the side of the sample 50 between the cover 340 and the base 360, between the washer 310 and the base 360, or both. The sample holding device 300 can be configured to fit on a pressure generator used to apply pressure on the sample 50 with a fluid for deforming the sample 50. The sample holding device 300 can fit in narrow environments, enabling the observation of the sample 50 at tilted angles, which can enable observations with analytical techniques in a scanning electron microscope, such as EBSD, EDX, ECCI, and optical techniques, such as 3D DIC.

In a non-limiting example, the sample holding device 300 has a compact and miniaturized design, with the various components having a complementary configuration so they fit well together to prevent undesirable leaking or the like. In some instances, each of the cover 340 and the base 360 are approximately elliptical in shape, and in other instances each of the cover 340 and the base 360 are approximately circular in shape, although other shapes are possible. While various dimensions are likewise possible, a height can be approximately in the range of about 2 millimeters to about 10 millimeters, and in some embodiments it is approximately 5 millimeters, or even less, and a diameter can be approximately in the range of about 20 millimeters to about 50 millimeters, and in some embodiments it is approximately 32 millimeters, or even less. The sample holding device 300 enables observation of the sample 50 from a wide range of angles. For example, up to approximately 70 degrees (i.e., looking from the side), or less, and from a very short distances, such as approximately in the range of about 1 millimeter to about 10 millimeters from a closest portion of a perimeter of the device, and in some instances approximately 5 millimeters from a closest portion of a perimeter of the device. The design of the sample holding device 300 can also limit air entrapment under the sample 50 when fitted on the pressure generator, even with a deformed sample. In some instances, the shape of the opening 361 in FIG. 2B can prevent air from being entrapped under the sample 50 when the sample holder 300 is immersed in a bath of fluid in a tilted position. In some configurations, one side of the opening 361 can be in the fluid while the air present under the sample 50 can still have a path to be evacuated. In some embodiments, a part (e.g., top element 530 of FIG. 5) can be attached to the top of the sample holder 300 such that only a bottom portion of the sample holding device 300 is immersed in fluid while keeping a top part of sample 50 predominantly or fully dry before performing experiments. Exemplary materials for use in forming the cover 340 and the base 360 include but are not limited to precipitation-hardened 17-4 stainless steel and/or high strength titanium alloys.

FIGS. 3A and 3B are exploded view illustrations of the sample holding device 300 of FIGS. 2A and 2B. FIGS. 3A and 3B show the arrangement of the washer 310 and sample 50 between the cover 340 and base 360 of the sample holding device 300. FIG. 3A shows that the washer 310 can include one or more clamping ends or tabs 313 for clamping between the cover 340 and base 360 outside of the sample 50. The inside of the base 360 can include one or more grooves 362 for one or more seals or o-rings and one or more receiving ends or recesses 363 for receiving the tabs 313 of the washer 310. Also shown are exterior threads 369 of the base 360 that can be configured to be threadingly engaged with interior threads 349 of the cover 340. In operation, the sample 50 and washer 310 can be disposed on the base 360 and the cover 340 can be threaded onto the base 360 to complete the assembly of the sample holding device 300, as explained in more detail below.

Figure 3C:
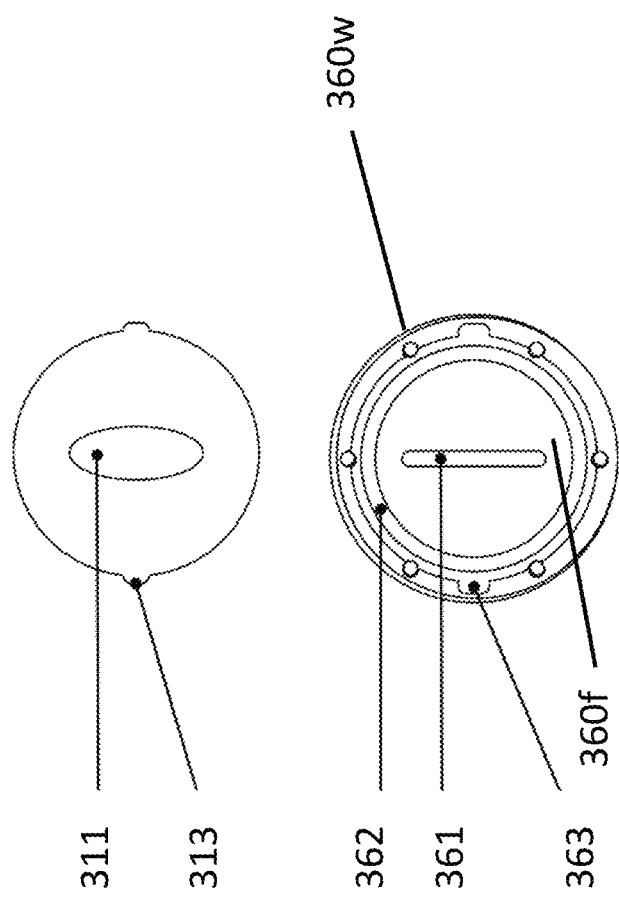
FIG. 3C is a top view of a washer and a base of the sample holding device of FIG. 2A.

FIG. 3C is an illustration of a washer 310 and base 360 of the sample holding device 300, more clearly showing the relationship between the tabs 313 of the washer and the recesses 363 in the base 360 for receiving the tabs 313. A person skilled in the art will recognize other coupling features can be utilized in lieu of, or in conjunction with, a male member like the tabs 313 and a female member like the recesses 363 without departing from the spirit of the present disclosure, and in some instances the male and female locations can be interchangeable provided the reciprocal element is provided on the other component.

Figure 3D:
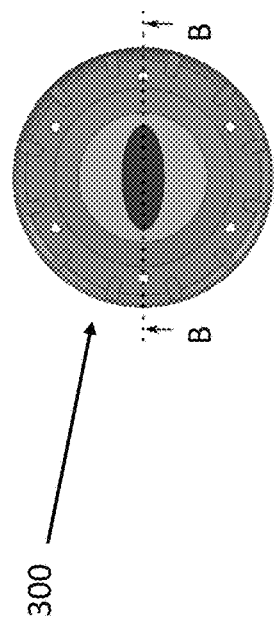
FIG. 3D is a top view of the sample holding device of FIG. 2A.
Figure 3E:
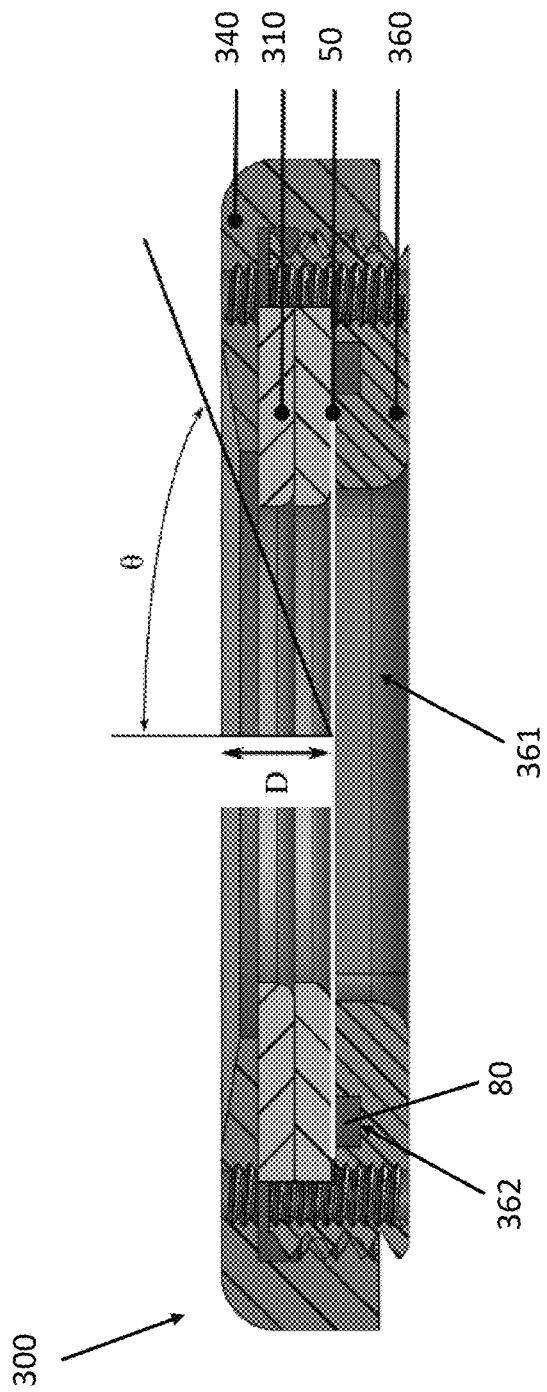
FIG. 3E is a cross-sectional view of the sample holding device of FIG. 3D taken along line B-B.

FIGS. 3D and 3E are top view and cross-sectional views, respectively, of the sample holding device 300. FIG. 3D is a top-down view of the assembled sample holding device 300, and FIG. 3E is a cross-sectional view of the assembled sample holding device 300 of FIG. 3D taken along line B-B. FIG. 3E shows the cover 340 can be screwed onto the base 360 until a top surface of the washer 310 (illustrated here as two washers stacked together) engages with the cover 340 and a bottom surface of the washer 310 engages with the sample 50. The sample can be held against the inside surface of the base 360 by the washer 310, as well as against an O-ring 80 that can be disposed in the groove 362 of the base 360. In operation, when fluid is forced into the aperture 361 of the base 360, the sample can deform away from the base 360, and the O-ring 80 can prevent egress of the fluid into the sample holding device 300, including when a pressure-supplying fluid is supplied to the aperture 361.

Figure 4:
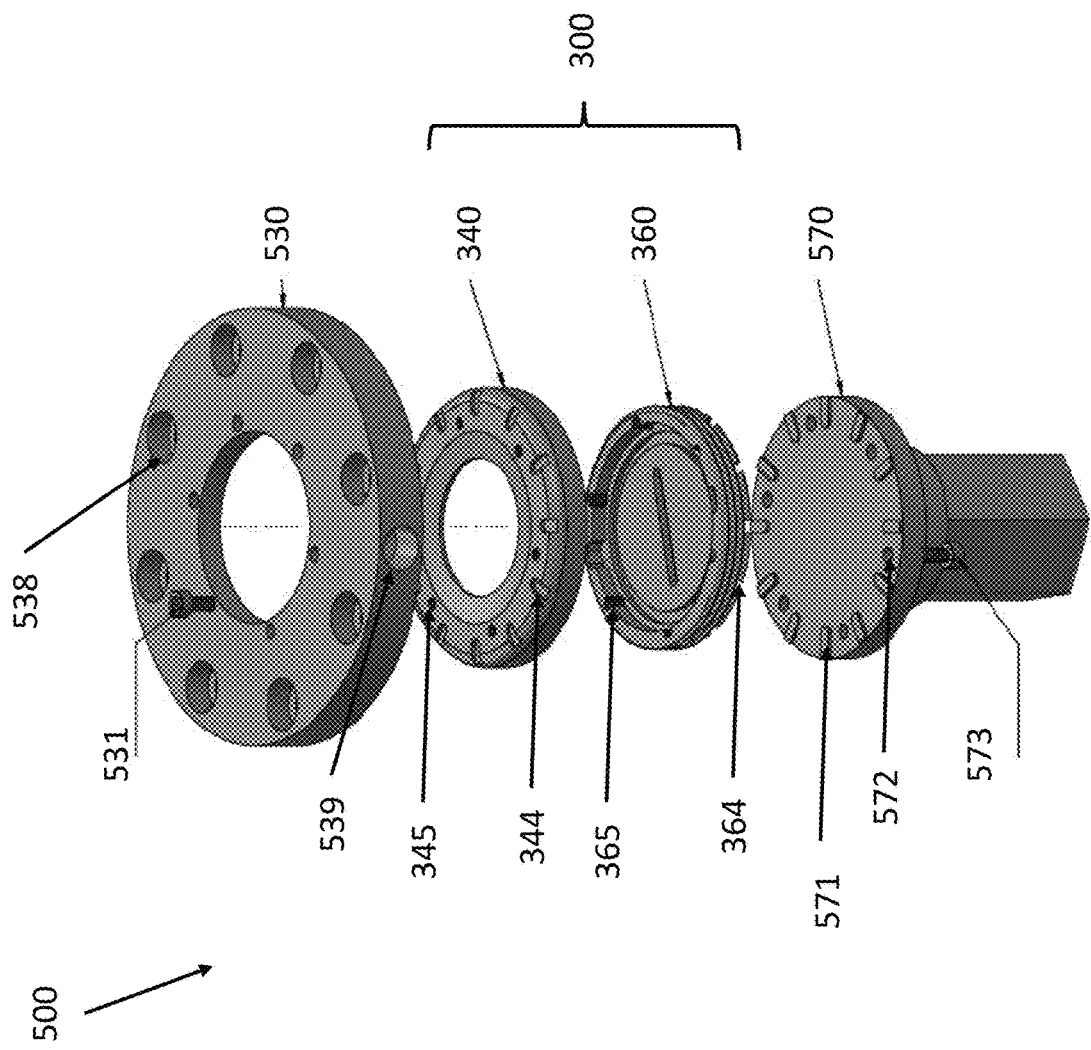
FIG. 4 is an exploded perspective view of one exemplary embodiment of an assembly base that can be used in conjunction with a sample holding device, the sample holding device as illustrated being the sample holding device of FIG. 2A.

FIG. 4 is an exploded view illustration of an assembly base 500 that can be used in conjunction with sample holding devices, such as the previously described sample holding device 300 and other such devices that can be made in view of the present disclosures. More particularly, FIG. 4 helps illustrate an assembly step for creating the sample holding device 300. As shown, the assembly base 500 can include a bottom platform 570 that can be configured to mate with the base 360 of the sample holding device 300 and a top element 530 that can be configured to mate with the cover 340 of the sample holding device 300 and facilitate assembly of the sample holding device 300. In operation, the base 360 can be engaged with the bottom platform 570. The bottom platform 570 can have a plurality of protrusions 571 that engage with corresponding recesses 364 in the bottom of the base 360 to locate the base 360 with respect to the bottom platform 570. Once located, one or more screws 573 can be inserted through the bottom platform 570, via holes 572 formed in the bottom platform 570, and threaded into threaded holes 365 in the base 360. This can cause the base 360 to be securely mated to the bottom platform 570. Once mated, an O-ring 80, sample 50, and washer 310 can be disposed onto the base 360 as described above.

With the washer 310 in place, the cover 340 can be threaded onto the base 360. A top element 530 can be mated to the cover 340 via protrusions (not visible, but similar to the protrusions 571 of the bottom platform 570 for example) that mate with corresponding recesses 344 on the top of the cover 340. One or more screws 533 can inserted through the top element 530, via holes 532 formed in the top element 530, and threaded into threaded holes 345 in the cover 340. Once attached, the top element 530 can assist in tightening the cover 340 to the base 360.

In some instances, the assembly base 500 can provide a convenient way to tighten the cover 340 into the base 360 because a high torque may be required to tighten the device 300 before testing. Also, in some instances, the hexagonal portion of the bottom platform 570 can be inserted in a fixed support featuring a corresponding hexagonal opening, while the top element 530 can be tightened with a spanner key or the like by inserting the spanner key into a hole 539 on the side of element 530 to apply the torque. The protrusion 571 and recess 344, 364 mating system can enable torque from the top element 530 to be transmitted to the cover 340 and from the bottom platform 570 to the base 360. The mating system can also ensure that, once the sample holder 300 has been tightened, screws 531 and 573 can be removed safely because no shearing forces were applied on them (i.e., they are not damaged). The assembly base 500 can also be used to untighten the sample holder 300 by applying torque in the opposite direction. In some embodiments, the top element 530 can also be used to fix the sample holder 300 onto the pressure-supplying device (not shown) during bulge-testing. In such use, the sample holder 300 can be tightened and fixed in the top element 530 with screws 531 or other fixation elements known to those skilled in the art. The ensemble, including the top element 530 and the sample holder 300, can then be screwed onto the pressure-supplying device, for example by way of eight screws going through the eight holes 538 of the top element 530. In some instances, the pressure-supplying device can have a sealing mechanism and the holes 538 in the top element 530 can therefore be used to accurately position the ensemble, including, or example, the top element 530 and the sample holder 300, on the sealing mechanism.

FIGS. 5A-5E are illustrations of washers having opening of different ellipticity. FIG. 5A shows a washer 611 with an opening 621 of elliptical ratio of approximately 1, which is approximately a circle. FIG. 5B shows a washer 612 with an opening 622 of elliptical ratio of approximately 0.8. FIG. 5C shows a washer 613 with an opening 623 of elliptical ratio of approximately 0.6. FIG. 5D shows a washer 614 with an opening 624 of elliptical ratio of approximately 0.4. And FIG. 5E shows a washer 615 with an opening 625 of elliptical ratio of approximately 0.2. In some instances, the washer 310 can have a thickness approximately in the range of about 0.5 millimeters to about 4 millimeters, and in some embodiments it can be approximately 1 millimeter. Likewise, in some embodiments the elliptical openings can have a fixed semi-major axis (denoted a in FIG. 6D) approximately in the range of about 4 millimeters to about 10 millimeters, and in some embodiments it can be approximately 6.5 millimeters. Exemplary materials for use in forming the washers include but are not limited to precipitation-hardened 17-4 stainless steel and/or high strength titanium alloys.

The sample holding device 300 can contain one or more of the washers 611-615 to control the strain in the sample 50 during deformation to create biaxial loading conditions. The use of multiple washers of different ellipicities enables the sample holding device 300 to create complex strain paths. Accordingly, the ability to swap one or more washers 611-615 in and out of the sample holding device 300 provides a flexible way to change the loading conditions without other changes to an experimental setup. Additionally, the tabs 313 and recesses 363 can be designed to avoid shear on the sample 50 during tightening. In operation, during tightening, the base 360 can be fixed and the cover 340 can be screwed onto the base 360. As a result, the cover 340 can be rotated and translated towards the base at the same time. At one point the bottom surface of the cover 340 can be in contact with the top surface of the washer 310 while the bottom surface of the washer 310 is in contact with the sample 50. The tabs 313 and recesses 363 can prevent the cover 340 from transmitting a rotating motion to the sample due to shearing forces between the sample 50 and the fix base 360. Thus, at least in part due to the tabs 313 and recesses 363, the washer 310 can be prevented from rotating inside the base 360 and only translational motion can then be transmitted from the washer 310 to the sample 50.

In some instances, the washers 611-615 have surface treatments, such as sand blasting, to increase friction between adjacent washers and the sample holding device 300. For example, sand blasting can be performed on the bottom surface of the washers 310 to increase friction between the washer 310 and the sample 50. This friction can prevent the sample 50 from slipping under the washer 310 when hydraulic pressure is applied on the central part of the sample 50. However, the top surface and the side surface of the washers 310 can be kept smooth to avoid too much friction with the base 360 and the cover 340 during the tightening step of the device 300. Although illustrated as ellipses having particularly elliptical ratios in FIGS. 5A-5E, a person skilled in the art will understand various other shapes and sizes that can be used to form the opening(s) of washer(s) used in conjunction with the devices, systems, and methods provided herein. Other shapes that can be used include but are not limited to triangles, squares, rectangles, polygons of any number of sides, and other shapes, including freeform shapes (i.e., an unclassified shape, which may be made to achieve a particular result). Further, when using more than one washer, additional shapes can be achieved by combining the shapes of two or more openings. When more than one washer is used, the washers can be rotated with respect to each other to provide for various shapes and sizes. The resulting shape can be described as a resulting shape of the opening 341 formed in the cover 340. An elliptical ratio that is achieved when using more than one washer can be different than 1:1.

The present disclosure allows for a kit to be provided that includes one or more bases (e.g., base 360), one or more covers (e.g., top cover 340), and a plurality of washers (e.g., washer 310), with the bases, covers, and washers having various configurations as provided for herein or as otherwise derivable from the present disclosure. For example, in some kits, there may be a single base and/or cover and a plurality of washers that are configured to create one or more complex strain paths for a sample disposed in a receiving chamber of the resulting base-cover combination. The various paths can be achieved by using one or more of the washers to change at least one of a shape and a size of an opening formed in the cover. In some other kits, there can be different configurations of bases and/or covers that can result in different shapes and sizes of openings formed in the cover(s) and/or can be adapted for use with various instruments (e.g., SEMs and other devices, such as light microscopes, optical or laser profilometers, RX diffraction devices, and micro and nano indentation devices. One or more of other components of the device, such as seals (e.g., o-rings), can also be included as part of the kit.

Figure 6A:
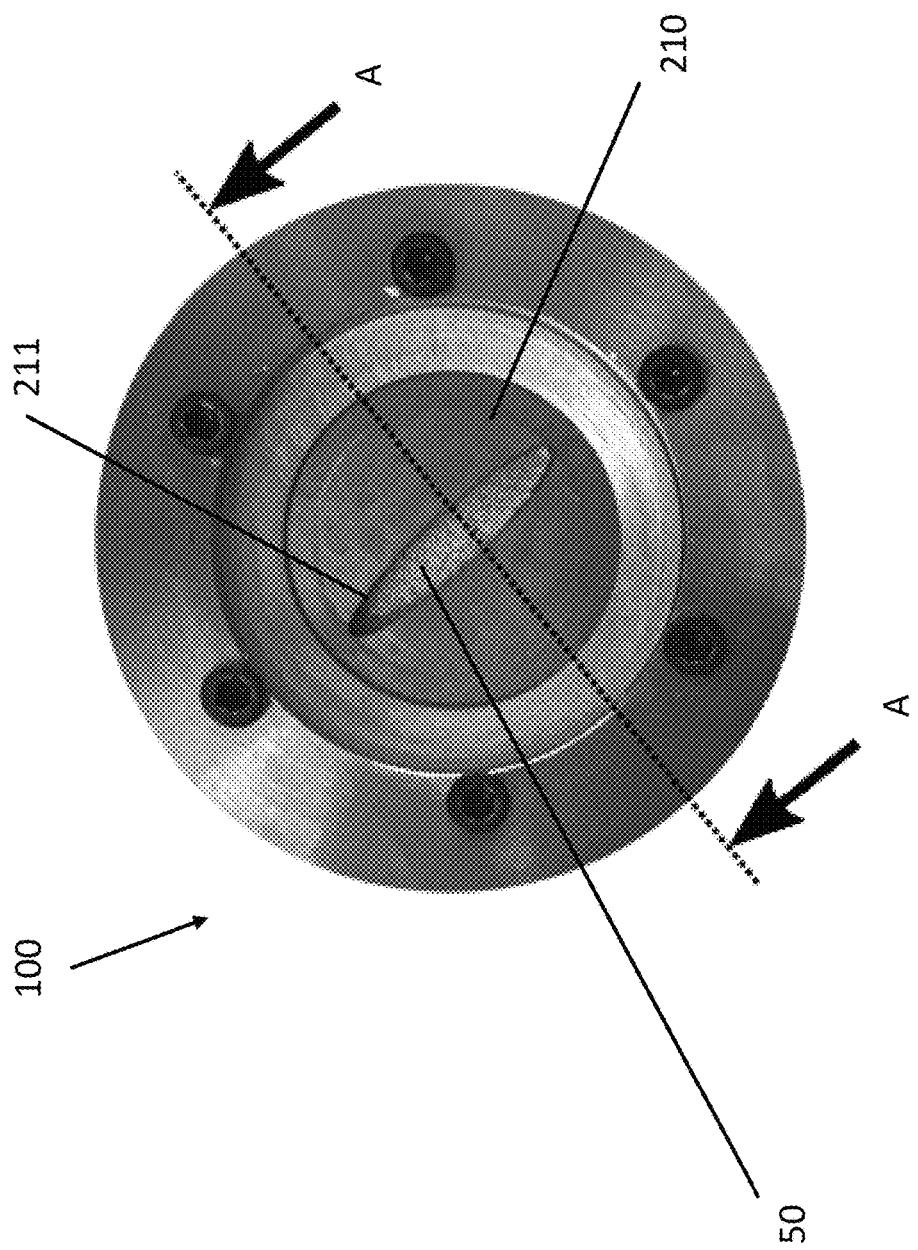
FIG. 6A is a top view of a sample holder that includes a material sample being held between a washer and a base.
Figure 6B:
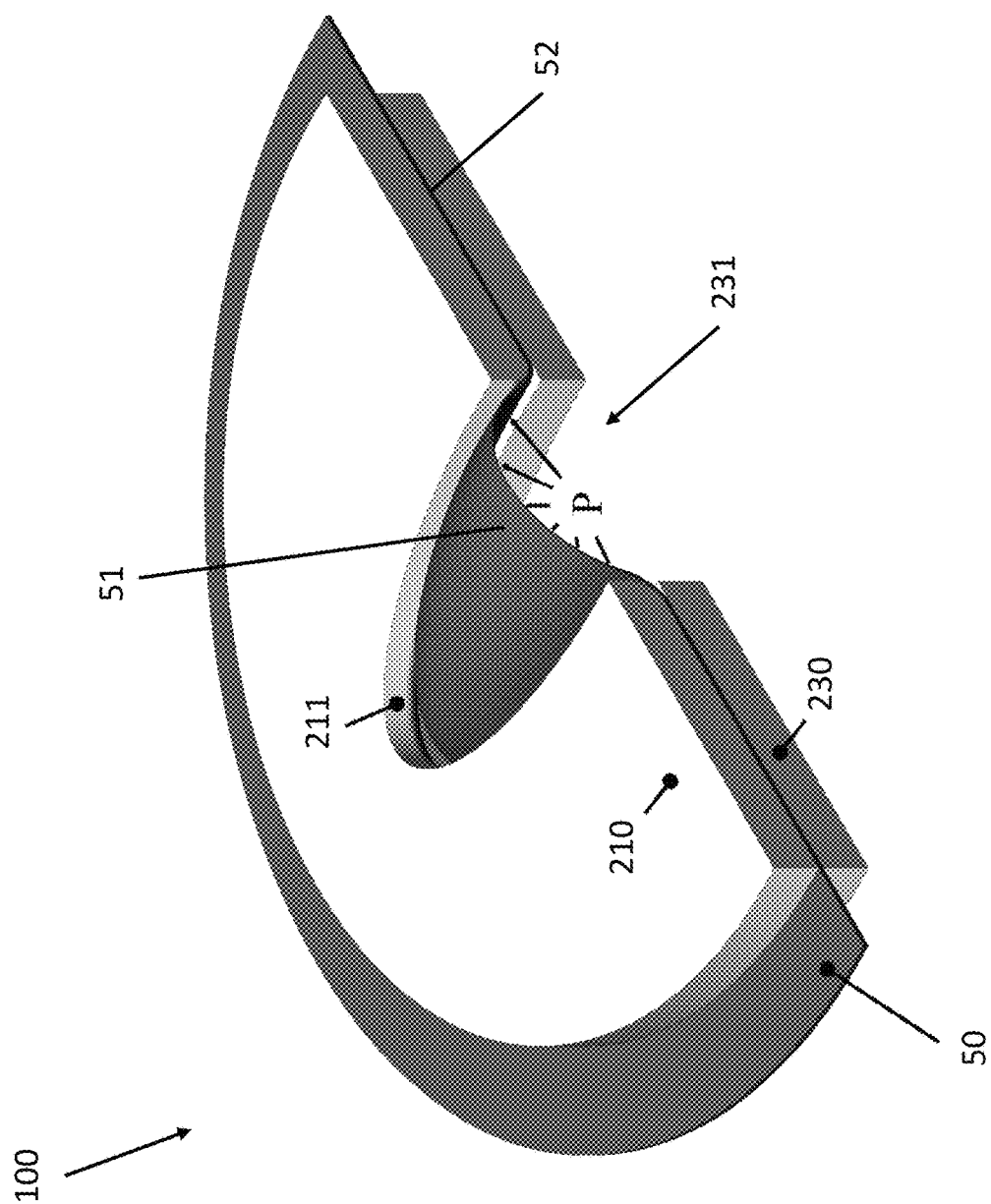
FIG. 6B is a cross-sectional view of the sample holder of FIG. 6A taken along line A-A, the material sample undergoing a bulge deformation test.

FIG. 6B is a schematic view of a deformation experiment based on the sample holder illustrated in FIG. 6A. FIGS. 6A and 6B provide an illustration of the sample holder 100 with a material sample 50 held between the washer 210 and the base 230 of the sample holder 100, with the sample 50 undergoing a bulge deformation test. A person skilled in the art will recognize such experiment(s) can be performed using the sample holder 300, and any other sample holder that can be derived from the present disclosures. The sample holder 100 includes the base 230 on which the sample 50 can be positioned, and the washer 210 can be disposed above the sample 50. The sample 50 can be clamped between the base 230 and the washer 210 by applying a clamping force with a cover (as described above with respect to the holder 300 of FIGS. 2A-3B) to a clamped portion 52 of the sample between the washer 210 and the base 230. In some instances, more than one washer 210 can be positioned above the sample.

The washer 210 includes an elliptical opening 211 to expose a portion of the sample 50. The base 230 includes a central opening 231 below the elliptical opening 211, through which hydraulic pressure P is used to push a central portion of the material of the sample 50 through an elliptical opening 211 in the washer 210 forming a bulge with an apex 51, as illustrated in FIG. 6B. The elliptical opening 211 around the apex 51 of the bulge of the sample 50 can be varied to impose strain paths ranging from equi-biaxial paths to plane strain. In some embodiments, a range of biaxial and complex strain paths that can be produced at the apex 51 of deformed samples 50 with aspects of the present disclosure. Strain and stress states at the apex 51 of the bulge of the sample 50 can be the focus, as this is the region where incremental EBSD observations can be carried out. In some instances, SEM imaging and ECCI can be used to track most parts of the sample 50 in the opening 211. In some instances, the foil transverse direction of the sample 50 can be aligned with the major axis of the elliptical opening 211.

Figure 6D:
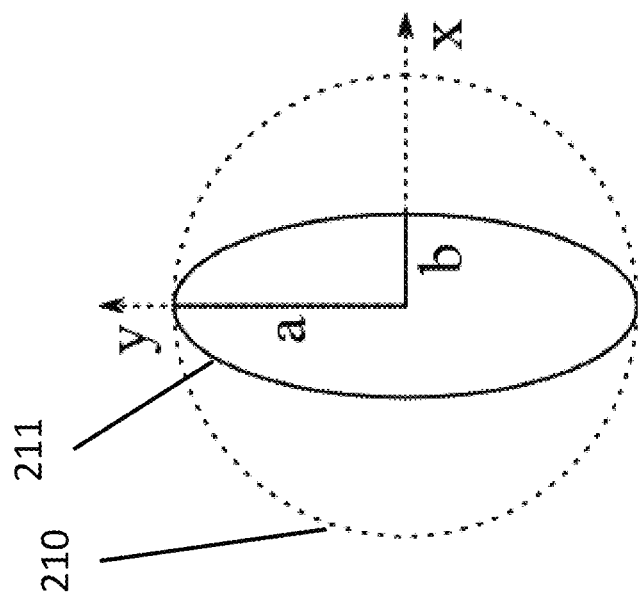
FIG. 6D is a top view of an elliptical opening of the washer of FIG. 6A.

Example washer 210 illustrates the elliptical ratio (b/a), which as described above with respect to FIGS. 5A-5E, can include values of approximately 1, approximately 0.8, approximately 0.6, approximately 0.4 and approximately 0.2, among other values, where b is the semi-minor axis, as illustrated in FIG. 6D. In some instances, the elliptic opening 211 of the washer 210 has a corner radius of to avoid stress concentration at the edge of the sample 50 (e.g., approximately 0.5 millimeters). In some instances, to prevent draw-in, the washer 210 can be sand-blasted to obtain a rough (approximately 10 micrometers) surface. The quality of the clamping can be evaluated after each test by comparing the external edge of the sample before and after the test using, for example, an optical camera.

In some instances, local shape and strain mapping can be used to calculate the stress state at the apex 51 of the bulged sample 50. In one example, a stereovision optical system can be used to perform strain mapping with the digital image correlation technique. Such measurements can also be achieved by using SEM-based 3D DIC and a pattern printed onto a top surface of the sample 50. In some instances, a masking technique can be used to apply a DIC pattern exclusively at the center of the sample 50 to, for example, keep the clamped areas 52 paint-free to avoid draw-in during the test. The masking process can include, for example, laser and engraving commercial masking tape to make individual masks with an opening approximately matching the elliptical opening 211 in the washer 210 used later during the test to adhere the samples 50 on a flat aluminum sheet. The masking opening can be precisely positioned at center of the sample 50, if desired, using markings engraved in the tape. White paint can be applied and a pattern of black ink can be deposited with an air brush. A pressure regulator can be used to adjust the mean size of black dots (for example, approximately 10 pixels in the optical images used for DIC) and to get a flat white-to-black intensity distribution. The mask can then be removed. In some instances, the mask can be configured to be easily peeled off.

Figure 6C:
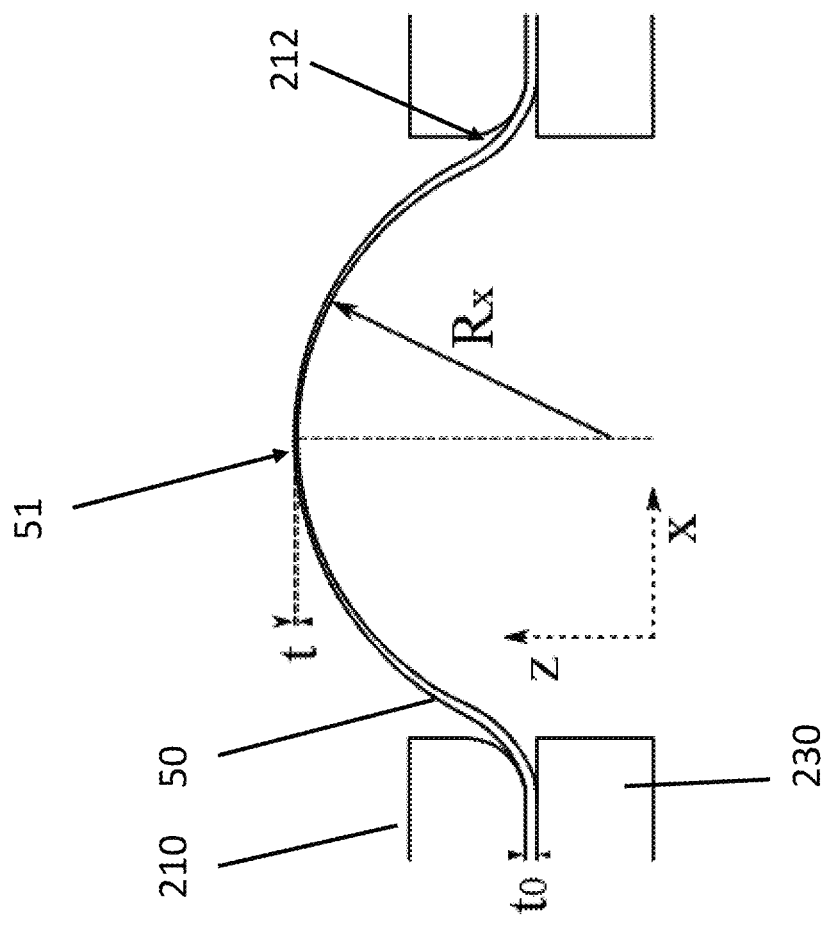
FIG. 6C is a schematic front view of the cross-sectional view of the sample holder of FIG. 6B.

FIG. 6C is a cross-section illustration of a material sample 50 held between a washer and a base and undergoing a bulge deformation test. The thickness at the apex 51 of the sample 50 is denoted t and the initial thickness of the foil t0. At the apex 51, R=1/c is the radius of curvature and α, the local curvature of the surface of the sample 50.

FIG. 6D is a schematic of an elliptical opening in a washer characterized by a semi-major axis and semi-minor axis. As described above, elliptical openings can be characterized by their semi-major axis a and semi-minor axis b.

FIGS. 6E and 6F are cross-section illustrations of difference bulge deformation tests. More particularly, FIG. 6E shows a sample holder 100 arrangement with a single washer 210 and the delivery of the hydraulic fluid 209 to through the opening 231 of the base 230 to deform the sample 50 against the elliptical opening 211 of the washer 210. FIG. 6F shows a sample holder 101 arrangement with a first washer 210 positioned above the sample 50 and a second washer 218 positioned above the first washer 210, with the second washer 218 having an opening 219 that is smaller than the opening 211 of the first washer.

A proportional stain path of a material 50 can be obtained using a single washer 210 in the sample holder 100, as shown in FIG. 6E. When two overlapping washers with a decreasing b values are used, as shown in FIG. 6F, the sample 50 can undergo a complex strain path. That is, the sample 50 bulge can deform in the strain path associated with the first washer 210 until it reaches the second washer 218, which can change the loading conditions towards a different strain path.

Complex strain paths can be obtained by using two overlapping openings with different elliptical ratio. FIG. 6F illustrates the material 50 first deforms along a first path defined by the opening 211 of the first washer 210 and then switches towards a second path with a different strain ratio defined by the second opening 219 of the second washer 218. A point of transition between the first path and the second path can be fixed, at least in part, by the thickness of the first washer 210 and the size of the opening 219 in second washer 218.

In operation, the generation of complex strain paths is a multi-step process which influences strain fields also far away for the central part of the sample 50. In a first step, the sample 50 deforms freely following the path imposed by the first washer 210. Then, the area around the bulge apex can start touching the lower surface of the second washer 218. Because the pressure required to deform a sample 50 through a small opening is high, the strain rate in the central part of the sample 50 can be significantly reduced while strain localization keeps building-up on the sides of the sample 50, that is, underneath the second washer 218 and along the ellipse major axis. The sample 50 forms the spherical surface that is gradually pushed against the bottom side of the second washer 218, letting the pressure increase in the chamber below the sample 50 until a central region of the sample 50 can flow (e.g., be deformed) into the second opening. Despite this complex process, in some experiments the central area of the sample 50 can undergo a sharp strain path transition with no significant shearing being observed.

In some instances, the strain ratio obtained with the second washer 218 can be different from the strain ratio observed with the same washer in a single proportional experiment. This gap can be explained by the difference in boundary conditions between the two tests: in the complex stain path experiment, the sample 50 can be lightly flowing at the edge of the opening 219, as opposed to being fixed in the conventional test. Because the sample 50 can be maintained by the hydraulic pressure against the bottom side of the second washer 218, complex strain paths can be efficiently generated when the difference in ellipse ratios between the first opening 211 and second opening 219 are high, i.e., with narrow second openings. In some instances, a strain ratio of approximately 2 can be obtained.

In use, a method of analyzing a sample (e.g., a metallic structure, such as a foil) can include disposing the sample in a holder, such as the sample holding device 300. The holder 300 can be coupled to a testing apparatus, such as a pressure supplying system, as well as to an SEM. A way to apply fluid pressure to the holder 300, such as via the aperture 361, can be associated with the holder 300, and a fluid pressure can be applied to the sample disposed in the holder 300. The fluid pressure can be from a fluid pressure system that is separately disposed from each of the holder and the testing apparatus, thereby allowing each of the holder, the testing apparatus, and the fluid pressure system can be easily disassociated from each other for use elsewhere. In other embodiments, the fluid pressure system can be incorporated as part of the testing apparatus. Application of the fluid pressure to the holder 300 can cause the sample to deform in a manner that is prescribed by a configuration of the holder 300. That is, based on the shape of the opening 341 of the cover 300, as modified by the washer(s) 311, the deformation is prescribed. Features of the sample can be subsequently observed, such as by looking through a side surface of the holder. Alternatively, or additionally, the sample can be removed from the holder and observed.

After an initial application of fluid pressure, the holder can be decoupled from the testing apparatus and the sample removed from the holder. A second sample (e.g., a metallic structure, such as foil, although the second sample can be different from the first ample) can be disposed in the holder, and the holder coupled to a testing apparatus. The testing apparatus may or may not be the same testing apparatus that was used for the first sample. In some instances, it can be a second testing apparatus. Either way, again a fluid pressure from a fluid pressure system can be applied to the holder, which can cause the second sample to deform in a manner prescribed by a configuration of the holder. The prescribed configuration can be the same or different from the first prescribed configuration. Features of the second sample can be subsequently observed, again such as by looking through a side surface of the holder and/or by removing the sample from the holder and observing it.

In some embodiments, after the first test is performed, rather than removing the sample, the holder can be decoupled from the first testing apparatus and coupled to a second testing apparatus. The second testing apparatus can then be operated in a manner that causes an effect on the sample, the sample having already previously been deformed by the first testing apparatus.

As described above, as part of the testing procedures, one or more washers can be rotated with respect to one or more of the base, the cover, the sample, and other washers if also disposed in the holder, to adjust the configuration of the holder, which in turn changes the way in which the sample deforms. In instances where more than one washer is disposed in the holder, a first washer can be rotated with respect to a second washer (and/or additional washers) to adjust the configuration of the holder, which in turn changes the way in which the sample deforms.

Figure 7:
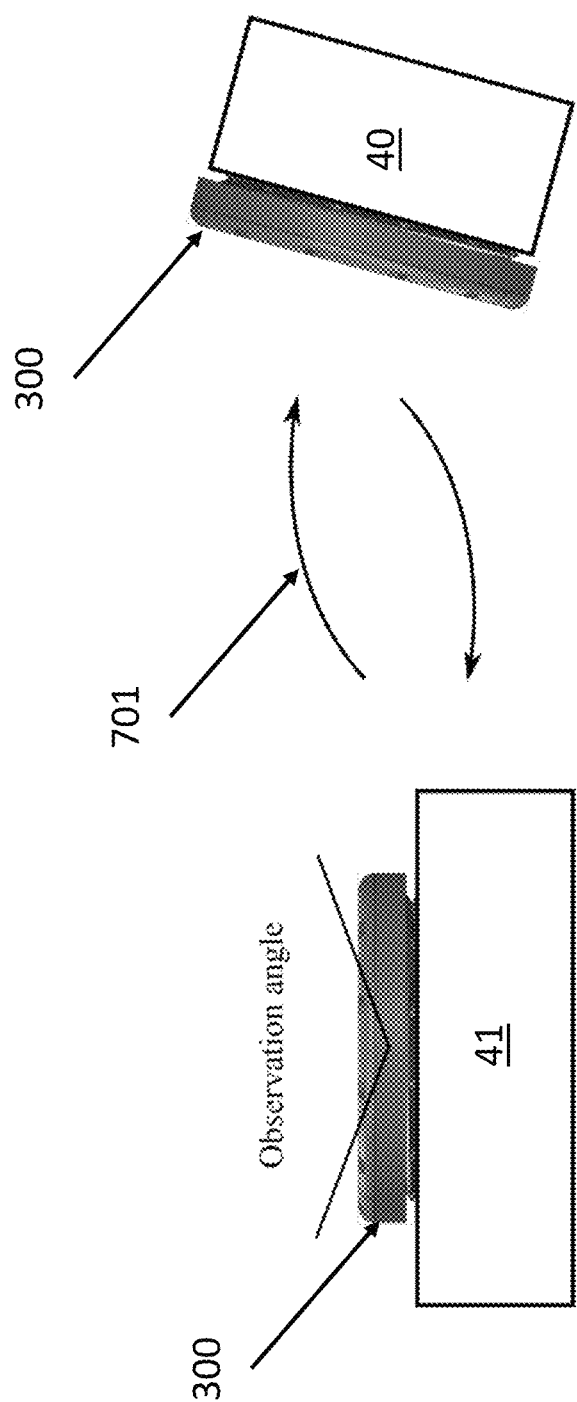
FIG. 7 is a schematic side view illustration of a method of using the sample holding device of FIG. 2A.

FIG. 7 is an illustration of a method of using the sample holding device 300. In operation, the sample holding device 300 can be placed on a testing apparatus 41 for supplying a fluid pressure to the sample 50 for conducting a deformation operation. Additionally, the sample holding device 300 can be placed on stage of an external device, such as an SEM stage 40 to conduct measurements of the sample 50. A person skilled in the art will understand many different ways by which the device 300 can be removably coupled to the devices 40, 41. The sample holding device 300 can be freely swapped between the devices 40, 41 (as indicated by arrowed 701) to conduct multiple incremental measurements of the sample 50 during one or more deformation operations.

One skilled in the art will appreciate further features and advantages of the disclosure based on the embodiments described in the present application. Accordingly, the disclosure is not to be limited by what has been particularly shown and described, except as indicated by the appended claims. All publications and references cited herein are expressly incorporated herein by reference in their entirety.

What is claimed is:

1. A device for holding a sample, comprising:
   a base having a floor and one or more walls that extend above the floor to form a receiving chamber for receiving a sample, the floor having one or more apertures extending therethrough for receiving a pressure-supplying fluid;
   a cover having a configuration that is complementary to at least a portion of the base such that the cover and base can be coupled together to tightly clamp a sample disposed in the receiving chamber, the cover having an opening extending therethrough; and
   one or more washers configured to be disposed between the base and the cover when the base and the cover are coupled together, each washer of the one or more washers having one or more openings extending therethrough that are configured to change at least one of a shape and a size of the opening formed in the cover, wherein each washer of the one or more washers comprises one or more clamping ends extending radially outward from a main body of the washer, the one or more clamping ends being configured to engage one or more complementary receiving ends disposed in at least one of the base and the cover.

2. The device of claim 1, further comprising one or more seals associated with the base, the one or more seals being configured to prevent device leakage when a pressure-supplying fluid is supplied to the one or more apertures.

3. The device of claim 1, wherein the cover is substantially transparent to allow for observation of a sample disposed in the receiving chamber when a pressure-supplying fluid is being applied to the one or more apertures of the base.

4. The device of claim 1, wherein a height of the device when the cover is coupled to the base to tightly clamp a sample disposed in the receiving chamber is between approximately two millimeters and five millimeters.

5. The device of claim 1, wherein a diameter of the device when the cover is coupled to the base to tightly clamp a sample disposed in the receiving chamber is between approximately 20 millimeters and 32 millimeters.

6. The device of claim 1, wherein an observation angle of the device when the cover is coupled to the base to tightly clamp a sample disposed in the receiving chamber is approximately 70 degrees or less.

7. The device of claim 1, wherein the one or more washers comprises a plurality of washers, and the one or more openings of a first washer of the plurality of washers and the one or more openings of a second washer of the plurality of washers have an elliptical ratio that is different than 1:1.

8. The device of claim 1, wherein the one or more washers comprises a plurality of washers that are configured to create one or more complex strain paths for a sample disposed in the receiving chamber.

9. The device of claim 1, wherein the base is configured to be mounted to a scanning electron microscope.

10. The device of claim 1, wherein the device is configured to be separately mounted from a pressure system that is configured to apply a pressure-receiving fluid to the one or more apertures of the base.

11. A kit, comprising:
   one or more bases, each base having a floor and one or more walls that extend above the floor to form a receiving chamber for receiving a sample, the floor having one or more apertures extending therethrough for receiving a pressure-supplying fluid;
   one or more covers, each cover having a configuration that is complementary to at least a portion of the one or more bases such that the cover and the one or more bases can be coupled together to tightly clamp a sample disposed in the receiving chamber, the cover having an opening extending therethrough; and
   a plurality of washers configured to be disposed between each base of the one or more bases and each cover of the one or more covers when the respective base and the respective cover are coupled together, each washer of the plurality of washers having one or more openings extending therethrough that are configured to create one or more complex strain paths for a sample disposed in the receiving chamber by changing at least one of a shape and a size of the opening formed in the cover, wherein each washer of the plurality of washers further comprises one or more clamping ends extending radially outward from a main body of the washer, the one or more clamping ends being configured to engage one or more complementary receiving ends disposed in at least one of the base and the cover.

12. The kit of claim 11, further comprising a plurality of seals configured to be associated with the one or more bases, the plurality of seals being configured to prevent device leakage when a pressure-supplying fluid is supplied to the one or more apertures.

13. The kit of claim 11, wherein at least one cover of the one or more covers is substantially transparent to allow for observation of a sample disposed in the receiving chamber of the one or more bases when a pressure-supplying fluid is being applied to the one or more apertures of the one or more bases.

14. The kit of claim 11, wherein a combined height of a base of the one or more bases and a cover of the one or more covers when coupled together to tightly clamp a sample disposed in the receiving chamber of the base is between approximately two millimeters and five millimeters.

15. The kit of claim 11, wherein a diameter of a cover of the one or more covers is between approximately 20 millimeters and 32 millimeters.

16. The kit of claim 11, wherein an observation angle of a device resulting from coupling a base of the one or more bases and a cover of the one or more covers to tightly clamp a sample disposed in the receiving chamber of the base is approximately 70 degrees or less.

17. The kit of claim 11, wherein the one or more openings of a first washer of the plurality of washers and the one or more openings of a second washer of the plurality of washers have an elliptical ratio that is different than 1:1.

18. A method of analyzing a metallic structure, comprising:
    disposing a metallic structure in a holder;
    coupling the holder to a testing apparatus;
    applying a fluid pressure from a fluid pressure system to the holder to cause the metallic structure disposed therein to deform in a manner prescribed by a configuration of the holder; and
    observing features of the metallic structure by looking through a side surface of the holder,
    wherein the fluid pressure system is separately disposed from each of the holder and the testing apparatus such that each can be disassociated from the other for use elsewhere.

19. The method of claim 18, further comprising:
    decoupling the holder from the testing apparatus;
    coupling the holder to a second testing apparatus; and
    operating the second testing apparatus to effect the metallic structure.

20. The method of claim 18, further comprising:
    selecting at least one washer and disposing the selected at least one washer in the holder to derive a desired configuration of the holder, the desired configuration of the holder being configured to achieve a desired metallic structure deformation.

* * * * *